US008608922B2

(12) United States Patent
Papadimitrakopoulos et al.

(10) Patent No.: US 8,608,922 B2
(45) Date of Patent: Dec. 17, 2013

(54) BIOSENSOR FOR CONTINUOUS MONITORING OF METABOLITES AND PROTEINS AND METHODS OF MANUFACTURE THEREOF

(75) Inventors: Fotios Papadimitrakopoulos, West Hartford, CT (US); Santhisagar Vaddiraju, Willimantic, CT (US); Faquir Chand Jain, Storrs, CT (US); Ioannis C. Tomazos, Vernon, CT (US)

(73) Assignee: The University of Connecticut, Farmington, CT (US)

( * ) Notice: Subject to any disclaimer, the term of this patent is extended or adjusted under 35 U.S.C. 154(b) by 922 days.

(21) Appl. No.: 12/614,893

(22) Filed: Nov. 9, 2009

(65) Prior Publication Data

US 2010/0116691 A1    May 13, 2010

Related U.S. Application Data

(60) Provisional application No. 61/112,218, filed on Nov. 7, 2008.

(51) Int. Cl.
*G01N 27/327* (2006.01)
(52) U.S. Cl.
USPC ............ 204/403.12; 204/403.01; 204/403.06; 204/403.07; 204/403.09; 204/403.1; 204/403.14; 600/347
(58) Field of Classification Search
USPC .................. 204/400, 403.1–403.15; 205/775, 205/777.5, 778, 792; 600/345–348
See application file for complete search history.

(56) References Cited

U.S. PATENT DOCUMENTS

| 4,418,148 A * | 11/1983 | Oberhardt ................. 204/403.11 |
| 5,030,333 A | 7/1991 | Clark, Jr. |
| 6,861,232 B2 | 3/2005 | Schaffar |
| 2009/0084678 A1* | 4/2009 | Joshi et al. ............... 204/403.14 |
| 2009/0101498 A1* | 4/2009 | Papadimitrakopoulos et al. ......................... 204/403.11 |

OTHER PUBLICATIONS

J.J. Burmeister, et al. "Self-Referencing Ceramic-Based Multisite Microelectrodes for teh Detection and Elimination of Interferences from teh Measurement of L-Glutamate and Other Analytes" Anal. Chem (2001) pp. 1037-1042; vol. 73, No. 5; American Chemical Society.
A.Guiseppi-Elie, et al. "Design of a Subcutaneous Implantable Biochip for Monitoring of Glucose and Lactate" IEEE Sensors Journal (Jun. 2005) pp. 345-355; vol. 5, No. 3; IEEE.
A. Heller "Implanted Electrochemical Glucose Sensors for the Management of Diabetes" Annu. Rev. Biomed. Eng. (1999) pp. 152-175; Annual Reviews.

(Continued)

*Primary Examiner* — J. Christopher Ball
(74) *Attorney, Agent, or Firm* — Cantor Colburn LLP

(57) ABSTRACT

A biosensor comprises a substrate; a reference electrode; a working electrode; a counter electrode; and a plurality of permeability adjusting spacers. The reference electrode, the working electrode and the plurality of permeability adjusting spacers are all being disposed to be substantially parallel to each other to create a plurality of enzyme containing porous sections. The enzyme containing porous sections contain an enzyme; where the enzyme is operative to react with a metabolite to determine the concentration of the metabolite. By combining a number of the aforementioned biosensors, the differential concentration of a target enzyme or protein is determined by monitoring the changes on its metabolite substrates.

43 Claims, 14 Drawing Sheets

(56) References Cited

OTHER PUBLICATIONS

S.M.Kirwan, et al. "Modifications of Poly(o-phenylenediannine) Permselective Layer on Pt—Ir for Biosensor Application in Neurochemical Monitoring" Sensors (2007) pp. 420-437; vol. 7; MDPI.

P.T.Kissinger, et al. "Voltammetry in Brain Tissue—A New Neurophysiological Measurement" Brain Research (1973) pp. 209-213; vol. 55; Elsevier Scientific Publishing Company, Amsterdam.

L.Lin, et al. "Novel Oxygen-Enhanced Membrane Assemblies for Biosensors"; Journal of Membrane Science (2006) pp. 173-180; vol. 278; Elsevier B.V.

R.C.Mercado, et al. "In Vitro and in Vivo Mineralization of Nafion Membrane Used for Implantable Glucose Sensors" Biosensors & Bioelectronics (1998) pp. 133-145; vol. 13, No. 2; Elsevier Science S.A.

F.Moussy, et al. "Performance of Subcutaneously Implanted Needle-Type Glucose Sensors Employing a Novel Trilayer Coating" Anal. Chem. (1993) pp. 2072-2077; vol. 65; American Chemical Society.

G. Nagy, et al. "A New Type of Enzyme Electrode: The Ascorbic Acid Elimnator Electrode" Life Sciences (1982) pp. 2611-2616; vol. 31; Pergamon Press.

W.H.Oldenziel, et al. "Evaluation of Hydrogel-Coated Glutamate Microsensors" Anal. Chem. (May 15, 2006) pp. 3366-3378; vol. 78, No. 10; American Chemical Society.

F. Patolsky, et al. "Long-Range Electrical Contacting of Redox Enzymes by SWCNT Connectors" Angew. Chem. Ed. (2004), pp. 2113-2117; vol. 43; Wiley-VCH Verlag, GmbH & Co.

J.Popp, et al. "Sandwich Enzyme Membranes for Amperometric Multi-Biosensor Applications: Improvement of Linearity and Reduction of Chemical Cross-Talk" Biosensors & Bioelectronics (1995) pp. 243-249; vol. 10; Elsevier Science Ltd.

J. Wang, et al. "Myoglobin-Containing Carbon-Paste Enzyme Microelectrodes for teh Biosensing of Glucose Under Oxygen-Deficit Conditions" Anal. Chem. (1999) pp. 5009-5011; vol. 71; American Chemical Society.

J.Wang, et al. "Evaluation of Different Fluorocarbon Oils for Their Internal Oxygen Supply in Glucose Micorsensors Operated Under Oxygen-Deficit Conditions" Analytica Chimica Acta (2000) pp. 187-192; vol. 411; Elsevier Science B. V.

Wilson, et al. "Biosensors for Real-Time in Vivo Measurements" Biosensors and Biolelectronics (2005) pp. 1-16; Elsevier B.V.

N.Sato, et al. "Amperometric Simultaneous Sensing System for D-Glucose and L-Lactate Based on Enzyme-Modified Bilayer Electrodes" Analytica Chimica Acta (2006) pp. 250-254; vol. 565; Elsevier B.V.

W.K. Ward, et al. "A Wire-Based Dual-Analyte Sensor for Glucose and Lactate: In Vitro and In Vivo Evaluation" Diabetes Technology & Therapeutics (2004) pp. 389-401; vol. 6, No. 3; Mary Ann Liebert, Inc.

* cited by examiner

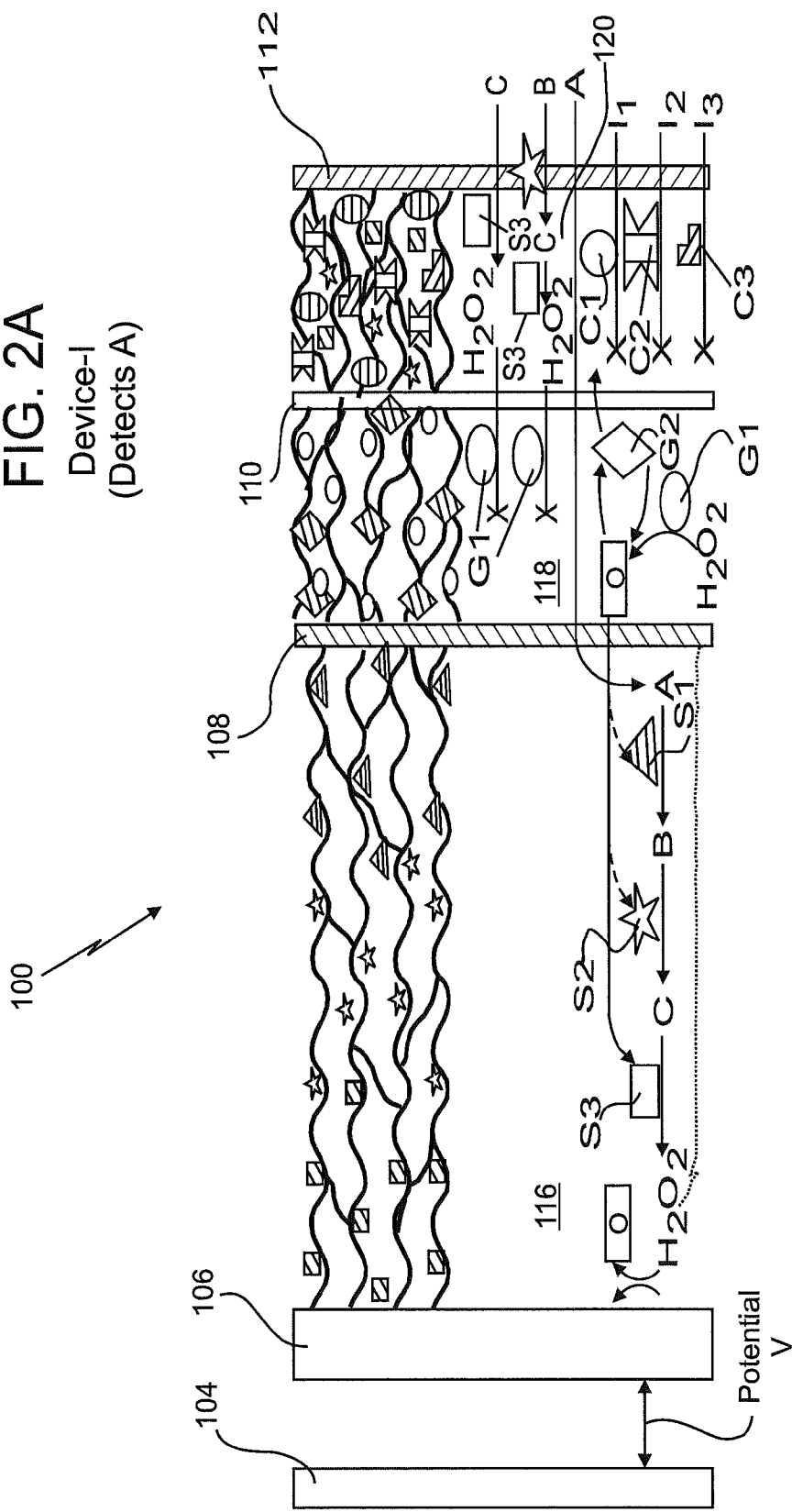

Device-II
(Detects A+B)

Device-III
(Detects A+B+C)

Device-IV (Detects B)

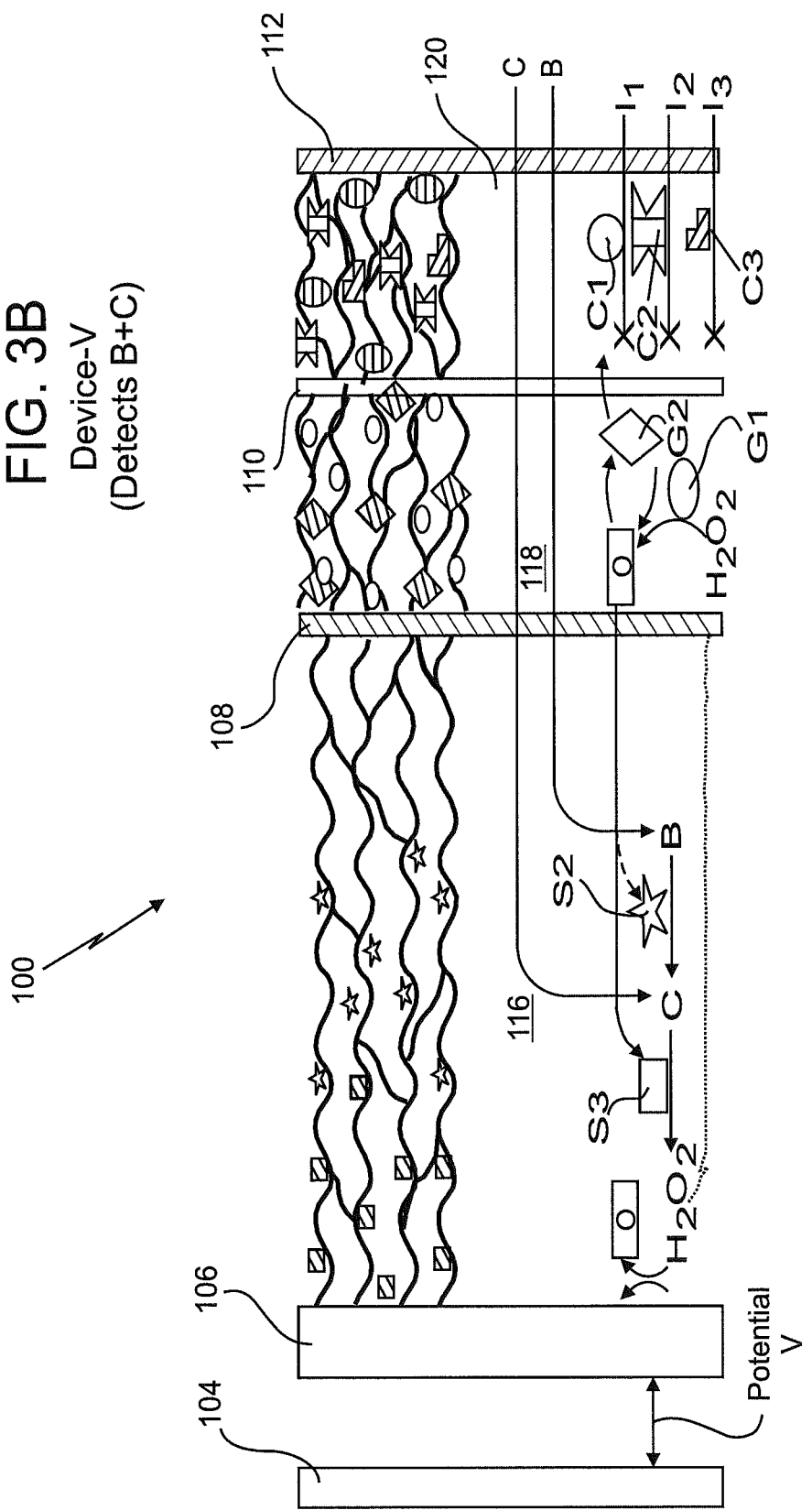

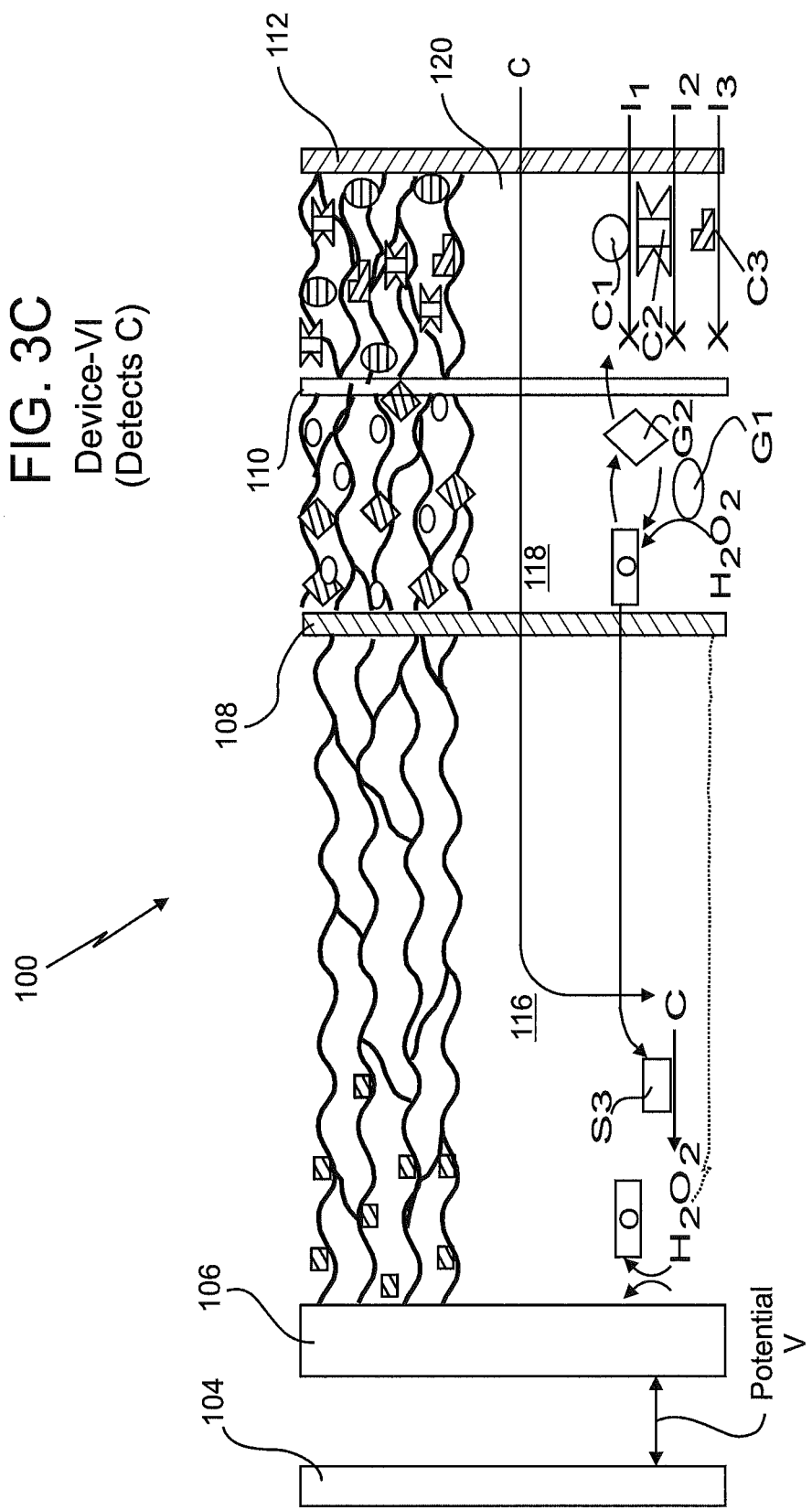

BIOSENSOR FOR CONTINUOUS MONITORING OF METABOLITES AND PROTEINS AND METHODS OF MANUFACTURE THEREOF

CROSS-REFERENCE TO RELATED APPLICATIONS

This application claims priority to provisional application 61/112,218 filed on Nov. 7, 2008, the entire contents of which are hereby incorporated by reference.

BACKGROUND

This disclosure relates to biosensors for continuous monitoring of metabolites and proteins and to methods of manufacture thereof.

The development of biosensors for continuous monitoring of various analytes in the body of a living being is important because of its potential to provide an early indication of various body disorders and diseases. An important class of biosensors are electrochemical sensors that link enzymatic reactions to electroactive products. These sensors can be readily miniaturized and have enabled the detection of very small volumes of analytes in clinical or in home-use settings. For example, the development of miniaturized implantable sensors for continuous monitoring of glucose has revolutionized the management and care of diabetes mellitus.

In many other clinical situations, it is desirable to monitor the concentration of various metabolites developed and released into the bodies of living beings such as, for example, lactate, creatinine, creatine, glutamate, phosphate, cysteine, homocysteine, and the like. For example, a device that can measure lactate levels can be used in the detection of a number of diseases and conditions (e.g., to indicate muscle fatigue, shock, sepsis, kidney disorders, liver disorders, congestive heart failure amongst others). In some clinical situations, simultaneous monitoring of two or more metabolites is desirable. Because of the complex interrelationship between glucose and other metabolic analytes it is often desirable to simultaneously detect glucose, glutamate, lactate, oxygen, carbon dioxide, and the like. Simultaneous monitoring of glucose, lactate and/or oxygen levels in the brain provides a comprehensive picture of complementary energy supply to the brain in response to acute neuronal activation. Levels of glucose and glutamate in cerebrospinal fluid are important in the control of diseases such as meningitis.

Currently, most of the electrochemical sensors used for the specific detection of lactate, glucose, glutamate, and the like, employ analyte-specific enzymes, and are based on the Clark-type amperometric detection.

For example, first generation Clark-type glucose sensors employ the glucose oxidase enzyme ($GO_x$), immobilized on top of a working electrode. This enzyme catalyses the oxidation of glucose to glucorolactone, as shown in reaction (1) below:

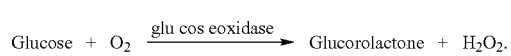
(1)

The generated hydrogen peroxide is amperometrically assessed on the surface of a working electrode according to reaction (2) below:

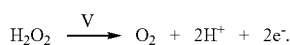
(2)

Clark-type bi-enzymatic sensors for detection of creatine employ two enzymes (namely creatinase and sacrosine oxidase) immobilized on top of the working electrode. First creatine is enzymatically converted by creatinase to sacrosine and urea (as shown in the reaction (3) below), the former of which is subsequently converted to glycine and hydrogen peroxide ($H_2O_2$) by the action of sacrosine oxidase enzyme (reaction 4).

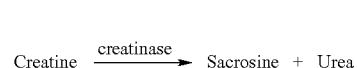
(3)

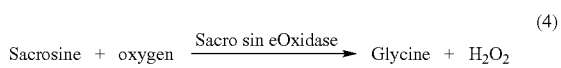
(4)

Similar to glucose sensors, the generated hydrogen peroxide is amperometrically assessed on the surface of working electrode by relating the current to creatine concentration. As is evident from reactions (1) and (4), optimum sensor performance can only be attained when the ratio of the substrate (i.e., glucose or sacrosine) to co-substrate (i.e., oxygen) is less than 1. If this ratio is greater than or equal to 1, the lack of oxygen renders reactions 1 or 4 oxygen-limited. This results in inaccurate readings of glucose and creatine, respectively.

In the case of glucose, a 0.18 mM oxygen concentration in the subcutaneous tissue is substantially lower than the 5.6 mM of physiological glucose concentration (i.e., glucose/oxygen ratio of ca. ~30). This leads to signal saturation at higher glucose concentrations. The onset of signal saturation is typically expressed as the apparent Michaelis-Menten constant, which defines the upper limit of the glucose range that the sensor can detect with enhanced confidence.

This issue has been addressed by the use of diffusion-limiting outer membranes that provide a greater permeability resistance to the larger sized substrate as opposed to the smaller sized co-substrate. As a result of this modification, semipermeable membranes based on NAFION®, polyurethane, cellulose acetate, epoxy resins, polyether-polyethersulfone copolymer membranes, and layer by layer (LBL) assembled polyelectrolytes and/or multivalent cations have been extensively investigated. However, in the use of semipermeable membranes it is desirable to have strict control over the thickness and uniformity of the outer membranes and this methodology comes at the expense of decreased sensitivity and increased sensor response time. Furthermore, the accumulation of exogenous reagents within these outer membranes (i.e., calcification, biofouling etc.) lead to sensor drift and therefore to their eventual failure.

In order to overcome this problem, an additional oxygen reservoir is provided within the outer membrane by incorporating oxygen-absorbing zeolites. Similarly, an oxygen reservoir (e.g., fluorocarbons, mineral oils and myoglobin) can be employed within the glucose oxidase enzyme layer to compensate for the decreased oxygen.

The eventual fabrication of multiple enzymatic Clark type sensors adjacent to each other necessitates a site specific deposition technique along with provisions to avoid crosstalk from one sensor element to another from the outward diffusing hydrogen peroxide. In all of the various methodologies described above, these provisions have not been implemented. Moreover, the growth of oxygen reservoir may be difficult to be implemented at will on a specific sensing element and not on another, since patterning of biological containing entities is at best challenging.

In another variation, second- and third-generation Clark type biosensors employ redox mediators and direct 'wiring' of enzymes to electrodes in an attempt to minimize the effects of oxygen concentration on the measurement of the analyte. In the case of mediators, their toxicity and biocompatibility along with the possibility to leach out from the device to the surrounding tissue present a major problem. Direct wiring of enzymes to electrodes minimizes these limitations, although adds unwanted complexities and higher expense.

The significant imbalance of glucose (as well as other analytes) to oxygen has prompted researchers to simultaneously measure substrate and co-substrate concentrations in order to account for co-substrate induced variations. Although this approach has its merits, this methodology is also prone to interferences from exogenous agents that render such calibration challenging.

Interferences from endogenous species (other than the primary substrate) generally originate from the fact that these species oxidize at the same potential as hydrogen peroxide. For example, in voltages of about 0.6 to about 0.7 volts (V) many endogenous species such as bilirubin, creatinine, L-cystine, glycine, ascorbic acid (AA), acetaminophen (AP), uric acid (UA), and the like, also get oxidized (leading to an erroneous electrochemical signal).

In order to increase confidence in sensing accuracy it is desirable to actively account for the signal generated by the endogenous species. At present not many methodologies have been developed to actively account for this. Anionic charged membranes (e.g., NAFION®, polyester sulfonic acid, cellulose acetate, and the like) have shown to exclude interferences from anionic species like ascorbic acid, uric acid, and so on, based on the principle of charge repulsion. These methods, however, inevitably impede permeation of negatively charged analyte species (e.g., lactate, pyruvate, glutamate, and the like), and render their detection challenging. In addition, the large response time associated with the diffusion of analytes through these membranes require long equilibration times in order to attain steady state performance between the inner and outer membrane, which is an additional drawback.

Another approach to eliminate interference signals from endogenous species has been the use of inner, ultra-thin, electropolymerized films between the working electrode and the enzyme layer. These films have been seen to partially screen analytes and analyte sensors from the interference agents. However, while these electropolymerized films minimize the contributions to signal from the endogenous species, they do not completely eliminate them.

In another approach, secondary enzymes (for example, ascorbate oxidase, which converts ascorbic acid to dehydroascorbate and water) have been incorporated in the outer membrane of the sensor to eliminate the particular species from reaching the electrode surface and contributing to the amperometric current. These secondary enzymes, do however, require oxygen as co-substrate and therefore have the potential of depleting the sensor of oxygen, which can negatively impact the operation of the primary enzyme.

Another major problem with the current state of the art biosensors is the unwanted production of byproducts as a result of enzymatic and/or electrochemical reactions. These unwanted byproducts tend to build up and/or adsorb on the surface of the working electrode leading to loss of function of the working electrodes. In some cases, the presence of these unwanted byproducts could also hinder the diffusion of analytes towards the working electrode as well as inhibit the progress of enzymatic reactions. For example, a lactate biosensor employing lactate oxidase works on the basis of the following reaction (5) below:

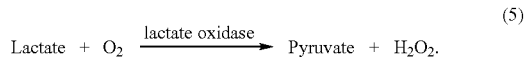

$$Lactate + O_2 \xrightarrow{lactate\ oxidase} Pyruvate + H_2O_2. \quad (5)$$

The generated hydrogen peroxide is amperometrically assessed on the surface of a working electrode by applying a positive potential, as shown above in reaction 2. However, because of the application of positive bias onto the working electrode, the negatively charged pyruvate (generated in reaction 5) tends to electrostatically adsorb on its surface leading to (i) taint the working electrode and subsequent loss of sensor sensitivity and (ii) inhibition of the reaction of lactate oxidase (reaction 5) with subsequent erroneous readings. To this end, higher applied potentials, double pulsed amperometry or pulsed amperometric detection have been the common strategies to renew the surface of the working electrode even though such techniques are complex to be applied for miniaturized sensors and implantable sensors with miniaturized driving electronics.

Because of its role to every metabolic activity of the body, the level of glucose is expected to vary following trauma, fever, exercise and/or another physical activities. Implantable glucose sensors can be made more reliable only when one takes into consideration the local and physiological variations in various metabolites that are in relation to glucose. These metabolites include oxygen, lactate and a number of proteins that take part in the glycolysis cycle. Some of these proteins also accelerate the generation as well as breakdown of various other body metabolites. While the levels of these body metabolites are indicative of the state of the body, in some case the activity of the proteins/enzymes itself is an indication of the state of the body. For example, the enzyme glutamic oxaloacetic transaminase (GOT), when found in elevated levels is an indicator of damage to liver (caused by viral hepatitis, heart attack, inflammation, alcohol abuse, and the like), as well as to pancreas, kidney, muscles and red blood cells due to injury.

A number of reports have also been disclosed for the fabrication and detection of glucose in conjunction with other metabolites. Similar to the glucose sensors, these more complex devices utilize outer semi-permeable membranes in order to account for interferences from oxygen and other endogenous species. In the detection of these metabolites it is generally desirable to perform a small number of sequential reactions in order to generate an electroactive species for electrochemical detection. Detection of proteins (enzymes as well as antibodies) is much more difficult and generally utilize enzyme linked immunosorbed assay (ELISA) methodologies. These methodologies are extremely difficult to be performed in-vivo and in a continuous manner. Developing methodologies to perform continuous protein detection in-vivo are therefore desirable for patients with a number of disorders.

SUMMARY

Disclosed herein is a measuring device for determining the concentration of metabolite in a sample media, comprising a working electrode; a reference electrode; a counter electrode; the working electrode is formed on a substrate; the working electrode is sequentially covered with multiple semipermeable layers constructed by either enzyme-containing porous sections or permeability-adjusting spacers; these permeability-adjusting spacers, are devoid of enzymes and function by controlling diffusion of various metabolites through adjacent enzyme-containing sections and/or inner and outer surfaces of the measuring device. The sequence of enzymatic reactions in conjunction with their permeability-adjusting spacers are such that a metabolite of interest is sequentially transformed in an electrochemical active species while electrochemically interfering metabolites are transformed into electrochemical inactive species. In parallel with this, the sequence of enzymatic reactions in conjunction with their permeability-adjusting spacers is also disposed to provide an adequate supply of co-substrates that are necessary for the aforementioned enzymatic reactions for both the detection of the metabolite of interest as well as the inactivation of interfering metabolites. This provides operative detection of a given metabolite while retaining high sensitivity and selectivity.

The spatial patterning of such a multi-layered working electrode to create a plurality of vertical cavities provide for the efficient diffusion outside the measuring device of the enzymatic byproducts that would otherwise build up and impair sensor functionality. Such vertical cavities can be backfilled with the appropriate set of enzymes to facilitate further byproduct degradation to smaller molecular weight substances that can diffuse outside the measuring device more easily from the multi-layered working electrode structure.

Alternative to the spatial patterning of the multi-layered working electrode, is the sequential growth of the layered enzymatic and semipermeable-spacer structures on pre-patterned working electrodes equipped with bottom-anchored vertical nanorods. Such a configuration also affords the incorporation of direct electron transfer to enzymes that simplifies a variety of metabolic pathways and eliminates the formation of a variety of byproducts.

Disclosed herein too is a method of the continuous determination of the activity of various body enzymes and proteins. Protein detection is achieved indirectly through deferential measurement of its metabolites. For this, a number of the aforementioned sensors is sequentially interrogated to determine the effect of target enzyme or protein to its metabolite substrates. Such biosensors can be used for continuous in vivo monitoring and diagnosis of various complex body disorders.

BRIEF DESCRIPTION OF THE FIGURES

With reference now to the figures where like parts are numbered alike:

FIG. 2 is a schematic representation of a multiple set of biosensors, along with various chemical, electro-chemical and diffusion processes that are used in the detection of protein levels through differential measurement of its metabolites. FIG. 2(A) shows the detection of the amount of metabolite A.

FIG. 3 is a continuation of FIG. 2 and is a schematic representation of a multiple set of biosensors, along with various chemical, electro-chemical and diffusion processes that are used in the detection of protein levels through differential measurement of its metabolites. FIG. 3(B) shows the detection of the amounts of the respective metabolites B and C or alternatively the sum of B and C. FIG. 3(C) shows the detection of the amount of the metabolite C;

DETAILED DESCRIPTION

Figure 1:
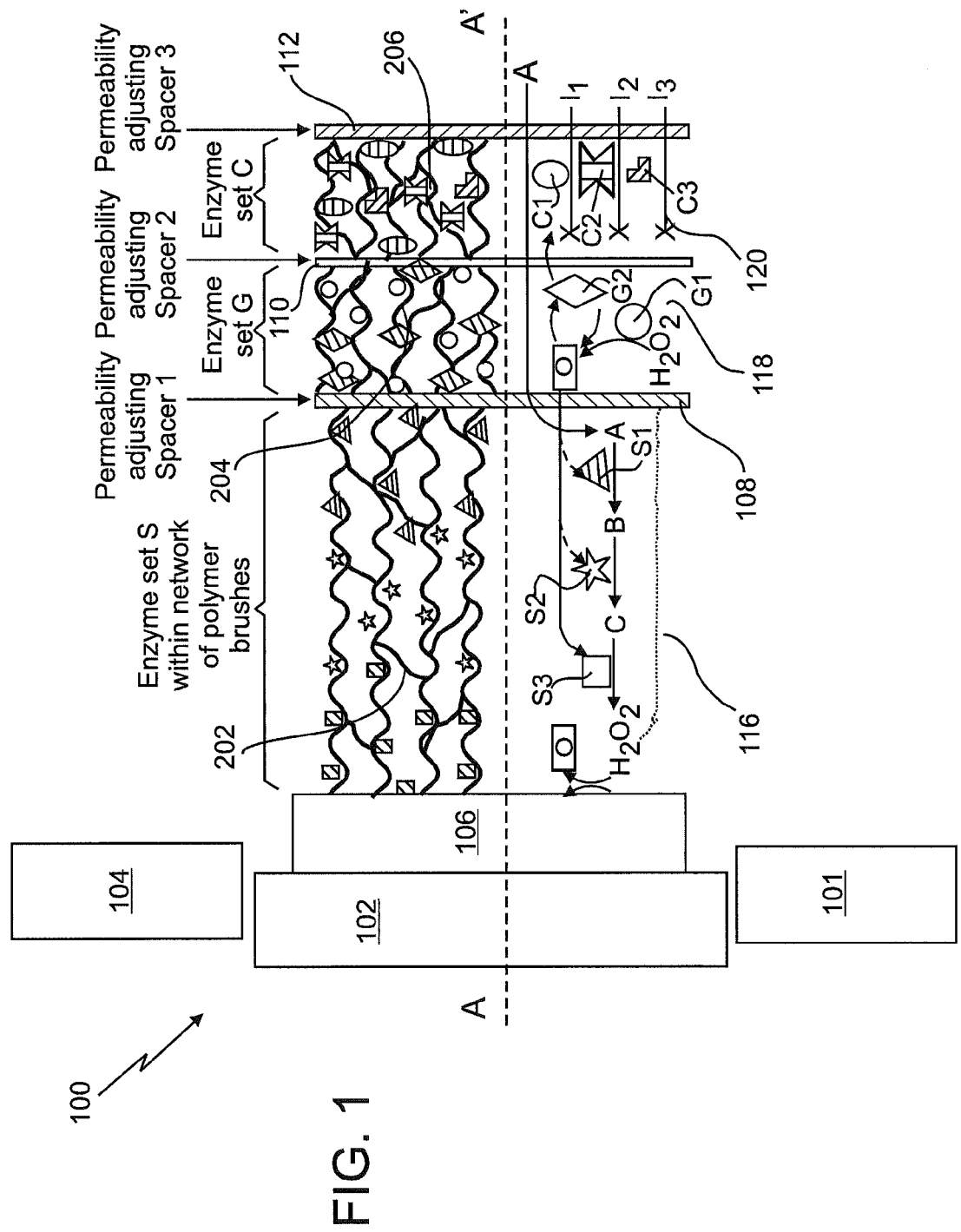
FIG. 1 is a schematic representation of an exemplary biosensor; the figure depicts various exemplary chemical, electro-chemical and diffusion processes associated with detection of a metabolite.

It is to be noted that as used herein, the terms "first," "second," and the like do not denote any order or importance, but rather are used to distinguish one element from another, and the terms "the", "a" and "an" do not denote a limitation of quantity, but rather denote the presence of at least one of the referenced item. Furthermore, all ranges disclosed herein are inclusive of the endpoints and independently combinable.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The transition phrase "comprising" is inclusive of the transition phrases "consisting essentially of" and "consisting of".

Disclosed herein is biosensor that actively permits determination of the concentration of a metabolite when disposed either inside the body of a living being (in-vivo) or outside the body. The biosensor comprises a working electrode, a reference electrode and a counter electrode. The working electrode is typically layered by a number of enzyme-containing porous sections and permeability-adjusting spacers. These permeability-adjusting spacers are generally devoid of enzymes and function by controlling diffusion of various metabolites thought adjacent enzyme-containing sections and/or inner and outer surfaces of the measuring device.

The enzymes advantageously perform numerous functions. In one embodiment, the enzymes react with metabolites to produce a detectable reactant that can be used to determine the amount of the metabolite in the body of a living being. In another embodiment, a plurality of enzymes react simultaneously or sequentially with the metabolites to determine the total amount of the metabolite in the body of a living being. In yet another embodiment, a plurality of second enzymes dissociate, decompose or degrade byproducts of a reaction between the metabolites and the first set of enzymes to produce products that either co-substrates to the aforementioned plurality of enzymes or are of a low enough molecular weight that can be readily removed from the biosensor.

The sequence of enzymatic reactions (in conjunction with their permeability-adjusting spacers) occurs in such a fashion that the metabolite of interest is sequentially transformed into an electrochemical active species while electrochemically interfering metabolites are transformed into electrochemical inactive species. Simultaneously, in parallel with these reactions, the sequence of enzymatic reactions in conjunction with their permeability-adjusting spacers are staged in a manner so as to provide an adequate supply of co-substrates that are desirable for the aforementioned enzymatic reactions for both the detection of the metabolite of interest as well as the inactivation of interference metabolites. In addition, the incorporation of the appropriate set of enzymes can also facilitate further degradation of interfering byproducts to lower molecular weight species. These byproducts originate from the enzymatic reactions of the metabolite that is being monitored. This facilitates the ease of byproduct diffusion to the outside of the measuring device (e.g., the biosensor) that would otherwise inhibit the inward diffusion of the electroactive species to be sensed on the working electrode. This cooperative action of the aforementioned enzymatic reactions provides operative detection of a given metabolite while retaining high sensitivity and selectivity in the measuring device.

The various enzymes employed in the disclosed biosensor may be broadly categorized into four sets of enzymes—a first set of enzymes (S) that reacts with metabolites to produce detectable reactants that are disposed on a working electrode to determine the amount of the metabolite present in the body of a living being; a second set of enzymes (G) that by itself or upon reacting with byproducts of the reaction between the metabolites and the first set of enzymes (S) or other metabolites that do not react with the first set of enzymes (S), generates a product which is the co-substrate for the reaction between the metabolites and the first set of enzymes (S); a third set of enzymes (C) that converts all active, electrochemical-interfering species into either to electroactive inactive species; and a fourth set of enzymes (R) that react with byproducts of the reaction between the metabolites and the first (S) and/or third (C) set of enzymes to decompose these byproducts into lower molecular weight species so that they can be removed or discharged from the biosensor.

The biosensor comprises of at least one working electrode with at least three sets of enzymes (S, G and C for sensing, generation of co-substrate and countering interferences, respectively), each of which are either disposed within enzyme-containing porous sections separated by permeability-adjusting spacers. In an exemplary embodiment, the enzyme containing section is a network of a polymeric material where enzymes are embedded. In another exemplary embodiment, this network of polymeric material comprises a polymer brush. These polymer brushes, if needed are adjusted such that they are permeable to certain chemicals (i.e., electro-active species, metabolites and metabolite intermediates) and less permeable to others (i.e., electro-active species, metabolites and metabolite intermediates). The biosensor is advantageous in that it comprises a by-product removal channel, which facilitates the removal of by-products from biosensor thus preventing erroneous readings of varying metabolite concentration.

With reference to the FIG. 1, the biosensor 100 comprises a substrate 102, a reference electrode 104, a counter electrode 101, and a working electrode 106 upon which is disposed a first permeability-adjusting spacer 108, a second permeability-adjusting spacer 110, a third permeability-adjusting spacer 112, a first enzyme containing porous section 116 disposed between the working electrode 106 and the permeability-adjusting spacer 108, a second enzyme containing porous section 118 disposed between the first permeability-adjusting spacer 108 and the second permeability-adjusting spacer 110 and a third enzyme containing porous section 120 disposed between the second permeability-adjusting spacer 110 and the third permeability-adjusting spacer 112. The first enzyme containing porous section 116, the second enzyme containing porous section 118 and the third enzyme containing porous section 120 each contain a network of polymeric materials, nanomaterials, or porous nanostructured inorganic matrices 202, 204 and 206, respectively. The network of polymeric materials, nanomaterials, or porous nanostructured inorganic matrices 202, 204 and 206 each contains enzymes, catalysts, and the like, that facilitates measurement of metabolites present in the body of a living being.

The biosensor 100 in the FIG. 1 contains two symbolic portions separated by an imaginary dotted line AA'. The portion above the imaginary dotted line AA' is a depiction of an exemplary biosensor 100 that contain the network of polymeric materials, nanomaterials, or porous nanostructured inorganic matrices (depicted by the curly lines) with the enzymes (depicted by triangles, stars and squares) disposed thereon while the portion below the dotted line AA' depicts the reactions occurring in the enzyme containing porous section during the determination of metabolite quantities. The reactions depicted below the dotted line show a metabolite A reacting with an enzyme S1 (depicted in the triangle) to produce a metabolite B that reacts with an enzyme S2 (depicted in the star) to produce a metabolite C that reacts with an enzyme S3 (depicted in the square) to produce a detectable reactant (e.g., an electroactive specie such as, for example, hydrogen peroxide) that decomposes to oxygen, protons and electrons when a bias potential (V) is applied between the working electrode 106 and the reference electrode 104. These electrons generate a change in current, which is proportional to the amount of the metabolite A. Thus the amount of the metabolite A in the body of a living being or in a media sample can be determined. In summary, the cascading reactions permit determination of the metabolite A in the body of a living being or in media sample. It is to be noted that the biosensor 100 can detect the presence of the metabolites either inside the body of the living being or alternatively outside the body, if the metabolites are brought into contact with it.

The first permeability-adjusting spacer 108, the second permeability-adjusting spacer 110 and the third permeability-adjusting spacer 112 are optional. The working electrode 106 is in electrical communication with the reference electrode 104 and is in operative communication with the first permeability-adjusting spacer 108, the second permeability-adjusting spacer 110 and the third permeability-adjusting spacer 112. In one embodiment, the working electrode 106 is in fluid communication with the first permeability-adjusting spacer 108, the second permeability-adjusting spacer 110 and the third permeability-adjusting spacer 112. In another embodiment, the first enzyme containing porous section 116, the second enzyme containing porous section 118 and the third enzyme containing porous section 120 are in fluid communication with one another. Each of the foregoing spaces 116, 118 and 120 are in fluid communication with fluids and metabolites that lie outside the biosensor.

The reference electrode 104 generally comprises silver/silver chloride and may be opposedly disposed to the working electrode 106. A biasing potential is applied between the reference electrode 104 and the working electrode 106 to produce a current. Changes in the current as a result of decomposition of the detection reactants (e.g., hydrogen peroxide) can be used to determine the amount of metabolites in the body of the living being into which the biosensor is placed.

The working electrode 106 is electrically conducting. The working electrode 106 can comprise a metal, a ceramic, a polymer, or a combination comprising at least a metal, a ceramic or a polymer. In one embodiment, the working electrode 106 generally comprises a metal. In an exemplary embodiment, the metal is an inert metal. Examples of the metal are platinum, gold, palladium, rhodium, iridium, or the like, or a combination comprising at least one of the foregoing metals. Metal nanoparticles in the form of nanotubes, nanorods, nanowhiskers, and the like can also be used to form the working electrode 106.

Suitable ceramics are indium tin oxide, tin oxide, indium zinc oxide, antimony oxide, or the like, or a combination comprising at least one of the foregoing ceramics.

Suitable polymers are intrinsically conducting polymers having conjugated double bonds such as polyacetylene, polypyrrole, polythiophenes, or the like, or a combination comprising at least one of the foregoing conductive polymers. Another example of an electrically conductive polymer is polyaniline that is neutralized with an acid. The electrically conducting polymers may be disposed upon an insulating substrate to form the working electrode 106

Alternatively, the working electrode 106 can comprise carbon. In one embodiment, the carbon can comprise carbonaceous nanoparticles (e.g., carbon black, graphene, single wall carbon nanotubes, double wall carbon nanotubes and/or multiwall carbon nanotubes). The carbonaceous nanoparticles and/or the metal nanoparticles can be compounded into a solid electrode by using an insulating binder. The combination of the binder and the nanoparticles is electrically conducting. In an exemplary embodiment, the working electrode 106 comprises a platinum metal sheet.

In one embodiment, the working electrode 106 has an area of about 0.01 square millimeters ($mm^2$) to about 100 $mm^2$. In a preferred embodiment, the working electrode 106 has a thickness of about 0.01 mm to about 0.5 mm. Alternatively, the area of the working can be smaller than 0.1 $mm^2$.

In another embodiment, the working electrode can comprise highly catalytic metal nanoparticles (i.e. platinum) that is disposed on the surface of gold electrodes. Such nanoparticles, although highly catalytic, are prone to electro-oxidize a variety of substrates including $H_2O_2$. In order to limit electro-oxidation to only $H_2O_2$, these electrodes are coated with a tight semi-permeable membrane such as electropolymerized poly(o-phenylene diamine) (PPD). PPD-coated electrodes membranes afford high selectivity against $H_2O_2$ but this selectivity comes at the expense of sensitivity. In order to remedy this problem, electropolymerization of PPD in the presence of a flavin mononucleotide (FMN)-wrapped single walled carbon nanotubes (SWNTs) is capable of retaining the original nano-platinum sensitivity while affording high selectivity for $H_2O_2$. In addition, owing to the large conductivity of SWNTs, such PPD/FMN-wrapped SWNT electropolymerized composite is capable of sequential growth of thick films, where a variety of enzymes can be hosted. Such sequential growth can provide the means to sequentially stack different enzymes according to a desired pattern. Such a pattern, for example, can be arranged to propagate a cascade of reactions for a given metabolite with a final target the production of $H_2O_2$. Such a reaction sequence can imitate part of metabolite catabolic reactions that stop at the production of $H_2O_2$. Such sequence of reactions can be stratified to produce $H_2O_2$ at the vicinity of the working electrode by proper enzyme stratification.

While the embodiment in the FIG. 1 refers to the first permeability-adjusting spacer 108, the second permeability-adjusting spacer 110 and the third permeability-adjusting spacer 112, it is possible for the biosensor to comprise a larger number of permeability-adjusting spacers (i.e., a plurality of permeability-adjusting spacers) that generally encompass a plurality of spaces 116, 118, 120, and the like, between them. In one embodiment, the first permeability-adjusting spacer 108, the second permeability-adjusting spacer 110 and the third permeability-adjusting spacer 112 each comprise a polymeric material that are permeable to certain chemicals while being impermeable to others.

In one embodiment, as depicted in the FIG. 1, the reference electrode 104, the working electrode 106, the first permeability-adjusting spacer 108, the second permeability-adjusting spacer 110 and the third permeability-adjusting spacer 112, are all disposed to be parallel to each other and to the working electrode 106. The reference electrode 104 is disposed adjacent to the working electrode 106. In addition, the first permeability-adjusting spacer 108, the second permeability-adjusting spacer 110 and the third permeability-adjusting spacer 112, are all disposed to adjacent to each other and with the first permeability-adjusting spacer being adjacent to the working electrode 106. In another embodiment, the first permeability-adjusting spacer 108 is disposed on top of the working electrode while the second permeability-adjusting spacer 110 and the third permeability-adjusting spacer 112 are disposed adjacent to each other on top of first permeability-adjusting spacer 108. The respective electrodes and the spacers do not need to be parallel to one another.

Examples of suitable polymeric materials that can be used in the permeability-adjusting spacers are thermoplastic organic polymers, thermosetting organic polymers and blends of thermoplastic organic polymers with thermosetting organic polymers. The polymeric material used in the spacer can be a homopolymer, a copolymer, a block copolymer, an alternating copolymer, an alternating block copolymer, a random copolymer, a random block copolymer, a graft copolymer, a star block copolymer, an ionomer, a dendrimer, or a combination comprising at least one of the foregoing polymers. The polymeric material may also be a blend of polymers, copolymers, terpolymers, or the like, or a combination comprising at least one of the foregoing types of polymeric materials.

Examples of thermoplastic polymers are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polyvinylchloride, polyvinyl acetate, humic acid, cellulose acetate, polythiophene, polyphenylene diamine, polypyrrole, polynaphthalene polyurethane, ethylene propylene diene rubber (EPR), polytetrafluoro ethylene, fluorinated ethylene propylene, perfluoroalkoxyethylene, polychlorotrifluoroethylene, polyvinylidene fluoride, polysiloxanes, or the like, or a combination comprising at least one of the foregoing organic polymers.

Examples of thermosetting polymers include polyurethane, natural rubber, synthetic rubber, epoxy, phenolic, polyesters, polyamides, silicones, or the like, or a combination comprising at least one of the foregoing thermosetting resins. Blends of thermosetting polymers as well as blends of thermoplastic polymers with thermosetting polymers can be utilized.

An exemplary polymer is an intrinsically conducting polymer made of poly(aniline), substituted poly(aniline)s, poly(pyrrole)s, substituted poly(pyrrole)s, poly(thiophene)s, substituted poly(thiophene)s, poly(acetylene)s, poly(ethylene dioxythiophene)s, poly(ethylenedioxypyrrole)s poly(p-phenylene vinylene)s, polycarbazoles, substituted polycarbazoles, polyindoles, poly(o-phenylene diamine) (PPD) or the like, or a combination comprising at least one of the foregoing intrinsically conducting polymers. It is to be noted that poly (o-phenylene diamine), poly(m-phenylene diamine) and poly (p-phenylene diamine) are all abbreviated as PPD.

The thickness of the respective permeability-adjusting spacers may be dependent upon the metabolite to be detected and the enzymes present in the respective spaces between the spacers. The respective permeability-adjusting spacers can be in the form of a film having a thickness of about 0.01 micrometers to about 1000 micrometers, specifically about 0.1 micrometers to about 100 micrometers, and more specifically about 1 micrometer to about 20 micrometers. The film can be manufactured by spin coating, drop casting, dip coating, knife coating, layer-by-layer assembly, inkjet printing, spray coating, by electropolymerizing the film, or a combination comprising at least one of the foregoing methods. An exemplary permeability-adjusting spacer 108, 110, 112 is in the form of a film and is manufactured by electropolymerization.

The electropolymerized film is obtained by applying a constant potential to a monomer-containing solution in an electrochemical cell. In one embodiment, the potential may be cycled during the manufacturing (e.g., deposition) of the electropolymerized film. The monomer is o-phenylene diamine, pyrrole, naphthalene, aniline, thiophene, phenyl, biphenyl, terphenyl, carbazole, furan, thiophene, fluorene, thiazole, pyridine, 2,3,5,6-hexafluorobenzene, anthracene, coronene, indole, biindole, 3,4-ethylenedioxythiophene, 3,4-ethylenedioxypyrrole, and both the alkyl and alkoxy derivatives of these aromatics, or the like, or a combination comprising at least one of the foregoing monomers. The monomer is immersed in a solution containing water-soluble oligomers.

The water-soluble polymers are polyethylene oxide, polyvinyl acetate, hydroxypropylcellulose, polyvinyl alcohol, polyhexaethyl methacrylate, polyallyl amine, poly(hyaluronic acid), chitosan, polysugars, polyitaconic acid, or the like, or a combination comprising at least one of the foregoing monomers. During the manufacturing of the electropolymerized film, the monomer concentration in the solution and the pH of the solution may be varied to obtain a film having the desired permeability properties. The electropolymerized film deposited on the electrode of the electrochemical cell may then be used as one or more of the permeability-adjusting spacers 108, 110, 112 in the biosensor 100.

Exemplary permeability-adjusting spacers 108, 110, 112 generally comprise an intrinsically conducting polymer. In another exemplary embodiment, the first permeability-adjusting spacer 108, the second permeability-adjusting spacer 110 and the third permeability-adjusting spacer 112 may comprise polyvinylchloride, polycarbonate, polyvinyl acetate, humic acid, cellulose acetate, polythiophene, poly(o-phenylene diamine), polypyrrole, polynaphthalene, polyaniline neutralized with a sulfonic acid or grafted with polyethylene oxide grafts, or the like, or a combination comprising at least one of the foregoing polymers.

In one embodiment, the first enzyme containing porous section between the working electrode 106 and the first permeability-adjusting spacer 108 can have a width of about 0.01 to about 1 micrometer. In another embodiment, the second enzyme containing porous section 118 disposed between the first permeability-adjusting spacer 108 and the second permeability-adjusting spacer 110 can have a width of about 0.01 to about 1 micrometers and the third enzyme containing porous section 120 disposed between the second permeability-adjusting spacer 110 and the third permeability-adjusting spacer 112 can have a width of about 0.01 to about 1 micrometers.

Disposed between the permeability-adjusting spacers 108, 110 and 112 and between the first permeability-adjusting spacer 108 and the working electrode 106 is a network of polymeric material. The network of polymeric material contains the enzymes that function to sense, generate a co-substrate and to counter interferences. These enzyme functions will be discussed in greater detail below.

The network of polymeric material may be a foam, a brush, an aerogel, or the like, or a combination comprising at least one of the foregoing. The foam may be nanoporous or microporous and can comprise any of the thermoplastic polymers, thermosetting polymers and/or intrinsically conducting polymers listed above. Combinations of the aforementioned polymers may also be used. The foam may have pores having sizes of about 1 nanometer to about 1,000 nanometers, specifically about 2 nanometers to about 500 nanometers, and more specifically about 10 to about 100 nanometers. Aerogels are generally manufactured from metal oxides, polymers, amorphous carbon, graphene, and carbon nanotubes, etc. and can comprise nanopores or micropores having the same dimensions as those of the foam listed above. The foam generally has a surface area of greater than or equal to about 100 square meters per gram ($m^2$/gm), specifically greater than or equal to about 500 $m^2$/gm, and more specifically greater than or equal to about 1,000 $m^2$/gm.

In an exemplary embodiment, the network of polymeric material is in the form of a polymeric brush. Polymeric brushes may comprise any of the thermoplastic polymers, thermosetting polymers and/or intrinsically conducting polymers listed above. Combinations of the aforementioned polymers may also be used.

A polymer brush consists of end-tethered (grafted, anchored) polymer chains stretched away from the substrate due to a volume-excluded effect. In mixed brushes, two or more different polymers grafted to the same substrate constitute the brush. Unlike unmixed brush polymers, different polymers in the mixed brush segregate into nanoscopic phases. The phase segregation is a lateral segregation process in a nonselective solvent in which different polymers form spherical or elongated clusters. Both the polymers are exposed on the top of the brush. In selective solvents, the mixed brush structure may be seen as a combination of lateral and layered segregation mechanisms. In the latter case, one polymer preferentially segregates to the top of the brush, while another polymer forms clusters segregated onto the grafting surface. The most important difference of the mixed brush compared to the homopolymer brush is that not only the height and density profile but also the composition profile depends on the solvent quality. In other words, the surface composition of the brush is switched by a change in its environment.

Each brush has a first end that contacts the permeability-adjusting spacer and a second that is projected outward into the enzyme containing porous sections 116, 118 and 120 between the working electrode 106 and the permeability-adjusting spacer 108 or between the permeability-adjusting spacers 108, 110 and 112, respectively. Disposed in the porous polymer is an enzyme, and more specifically multiple enzymes.

In one exemplary embodiment, the network of polymer brushes comprises water soluble forms of intrinsically conducting polymers; the intrinsically conducting polymers being polyaniline, substituted polyanilines, polypyrroles, substituted polypyrroles, polythiophenes, substituted polythiophenes, polyacetylenes, polyethylene dioxythiophenes, polyethylenedioxypyrroles, polyp-phenylene vinylenes, polycarbazoles, substituted polycarbazoles, polyindoles, poly(o-phenylene diamine)s or a combination comprising at least one of the foregoing intrinsically conducting polymers. In one embodiment, the network of polymer brushes is a network of porous conductive materials; the network of porous conductive materials being realized by electropolymerization of o-phenylene diamine, pyrrole, aniline, aniline, sulfonated aniline, sulfonated thiophenes, flavin mononucleotide, carboxy-functionalized aqueously dispersed carbon nanotubes, flavin mononucleotide coated single wall carbon nanotubes, and aqueous dispersed nanoparticles with aniline functionalities.

In yet another embodiment, the network of polymer brushes is a network of porous conductive materials; the network of porous conductive materials being realized by electropolymerization of monomers; where the electropolymerized monomers are further grafted with a polyethylene oxide oligomer.

In one embodiment, the electropolymerization of the electropolymerized network of porous conductive materials is sequentially conducted in the presence of the desired enzyme or mixture of enzymes to lead in stratified layers of enzyme containing porous conductive materials.

In one embodiment, there are different types of brushes used in the enzyme containing porous sections 116, 118 and 120 respectively. A first brush 202 is used in the first enzyme containing porous section 116, a second brush 204 is used in the second enzyme containing porous section 118, while a third brush 206 is used in the third enzyme containing porous section 120. In one embodiment, the brushes can have the same chemical composition. In another embodiment, each brush can have a different chemical composition.

Each set of brushes has an enzyme disposed on it. In one embodiment, 2 or more enzymes are disposed on the brush. The enzyme is embedded in the network of polymer brushes. In one embodiment, the first brush 202 has a first enzyme S disposed upon it. The enzyme S is used for sensing and is embedded in the network of polymer brushes. A set of enzymes (e.g., a plurality of enzymes $S_1$, $S_2$, $S_3$, and so on) can be disposed on the first brush 202. As depicted in the FIG. 1, the enzyme S comprises at least one enzyme selected to initiate a series of reactions in which the analyte is detected by generating hydrogen peroxide, the electrochemical oxidation of which produces a current proportional to the concentration of the analyte.

In another embodiment, the second brush 204 has a second enzyme G for generation of a co-substrate. A co-substrate is a chemical specie that is used by an enzyme to carry out the conversion of metabolite of interest to a reactant species like hydrogen peroxide. For example, $O_2$ can be considered a co-substrate for the aforementioned enzyme reactions 1, 4 and 5. In an exemplary embodiment the second enzyme G for generation of co-substrate, comprise two or more enzymes, one of which is capable of storing oxygen and releasing it in oxygen deficient conditions, while the other is capable of generating oxygen. A set of enzymes (e.g., a plurality of enzymes $G_1, G_2, G_3$, and so on) can be disposed on the second brush 204.

In another embodiment, the third brush 206 has a third enzyme C disposed thereon, for countering interferences and comprises a mix of enzymes that initiate another series of reactions to convert an electrochemical active endogenous species like ascorbic acid, acetaminophen, uric acid, and the like, into an electrochemical inactive species. A set of enzymes (e.g., a plurality of enzymes $C_1, C_2, C_3$, and so on) can be disposed on the third brush 206. Because of the presence of these interference-rejecting enzymes in enzyme set C, the biosensor is capable of producing a response that only corresponds to the analyte of interest. Because of the presence of co-substrate storing and co-substrate generating enzymes in enzyme set G, the biosensor is also capable of working in co-substrate deficient conditions. The tunable nature of the permeability adjusting spacers affords the ability to control the permeability and thereby the sensitivity of the sensors.

The network of brushes with the enzymes disposed thereon can be deposited by any of the methods selected from techniques like drop casting, dip coating, knife coating, spin coating, spray coating, inkjet printing, and electrodeposition. A preferable method of deposition is electrodeposition that does not require post patterning in the x and y dimensions.

The enzymes in the first enzyme set S (i.e., $S_1, S_2, S_3$, and so on) are transferases, hydrolases, oxidases, peroxidases, kinases, superoxidases, phosphatases, or the like, or a combination comprising at least one of the foregoing enzymes, such that at least one of them initiates a reaction with the analyte of interest to produce hydrogen peroxide as the end product.

The enzymes in the second enzyme set G (i.e., $G_1, G_2, G_3$, and so on) are transferases, hydrolases, oxidases, peroxidases, kinases, superoxidases and phosphatases or the like, or a combination comprising at least one of the foregoing enzymes, such that at least one of them initiate a reaction converting hydrogen peroxide to the co-substrate (e.g., oxygen). It is also desirable for second enzyme set G to be capable of storing this co-substrate as well. In one exemplary embodiment, the second enzyme G comprise myoglobin (which can store oxygen) and catalase (which produces oxygen from $H_2O_2$) respectively.

The enzymes in the third enzyme set C (i.e., $C_1, C_2, C_3$, and so on) are transferases, hydrolases, oxidases, peroxidases, kinases, superoxidases, phosphatases, pyrophosphatases, oxygenases, nucleases, lipases, peptidases, transacetylases, hydroxylases, dioxygenases, dehydrogenases, carboxylases, aminases, catalases, phosphohydrolases, diaminases, reductases, synthases, kinases, caspases, methionine synthase, cystathionases, or the like, or a combination comprising at least one of the foregoing enzymes, such that at least one of them initiates a reaction that converts the electroactive interfering endogenous species ($I_1, I_2, I_3, \ldots I_n$) to non-electroactive ones.

The permeability-adjusting spacers 108, 110, 112 or the working electrode 106 with the brushes disposed thereon are manufactured via electropolymerization-based fabrication. In one embodiment, the enzyme embedded network of polymer brushes are deposited by immersing the working electrode in a buffer solution containing the monomer and the appropriate enzyme(s). The concentration of the monomer can be varied and the monomer is ortho-phenylene diamine, para-phenylene diamine, meta-phenylene diamine, pyrrole, naphthalene, aniline, thiophenes, sulfonated aniline, sulfonated pyrrole, phenols, flavins, or the like, or a combination comprising at least one of the foregoing monomers.

Chemical modification of these electropolymerized monomers with polyethylene oxide (PEO), polyvinylacetate, polyhydroxyethylmethacrylate, poly(allyl amine), and other water soluble oligomers or pre-polymers can provide a more loosened brush like configuration. Here mono-, bi-, and multi-functional decoration of these water-soluble oligomers and pre-polymers can assure crosslinked-assisted immobilization. In order to extend the electropolymerization thickness (es) of these networks, soluble mediators (that can be later washed off) or high aspect ratio electroactive nanostructures (i.e., nanocrystals, nanotubes, nanowires, and nanoplatelets (i.e., graphene, carbon nanotubes, and the like)) can be employed. Attaining structural irregularity of the electropolymerizing moiety(ies) is (are) important to vary the porosity of the network of polymer brushes. Electropolymerization is achieved by applying a bias to the working electrode for a fixed amount of time, following which the electrode is washed in distilled water or a buffer solution.

In an exemplary embodiment, the network of polymer brushes upon which the enzymes are disposed can be further embedded with nanomaterials and conducting polymers so that the biosensor can be used to probe the local pH. Because of the redox nature of these nanomaterials and conducting polymers, any change in pH is registered as change in the potential between the reference and the working electrode. This change in potential can be accessed and can be correlated to changes in the local pH. In another exemplary embodiment, the permeability-adjusting spacers 108, 110 and 112 can be embedded with nanomaterials and conducting polymers so that the biosensor can be used to probe the local pH.

In another exemplary embodiment, the enzymes can be contained in a matrix of nanosized materials, such as networks of carbon nanotubes, flavin mononucleotide coated single wall carbon nanotubes, porous graphene, porous zirconium phosphonate matrices, as well as nanoporous matrices formed by inorganic nanoparticles, nanorods, nanotubes, nanoplatelets, and nanohorns, or combinations thereof.

In another exemplary embodiment, the network of polymer brushes can be deposited after the deposition of the respective enzyme sets. These network of polymer brushes as well as the enzymes can be deposited by any of the methods selected from techniques like drop casting, dip coating, knife coating, spin coating, spray coating, electrodeposition, electropolymerization, layer by layer assembly, inkjet printing, and screen printing. In one embodiment, at least one of the first enzyme containing porous section, the second enzyme containing porous section and the third enzyme containing porous section and/or the first permeability adjusting spacer, the second permeability adjusting spacer and the third permeability adjusting spacers can be deposited by spin coating, drop casting, dip coating, knife coating, spray coating, inkjet printing, or electropolymerization. In an exemplary embodiment, when o-phenylene diamine is used to manufacture at least one of the first enzyme containing porous section, the second enzyme containing porous section and the third enzyme containing porous section and/or the first permeability adjusting spacer, the second permeability adjusting spacer and the third permeability adjusting spacer, the electropolymerization of o-phenylene diamine is performed at different pHs.

In yet another embodiment, the network of polymer brushes upon which the enzymes are disposed are not separated by permeability-adjusting spacers. In yet another embodiment, the enzyme sets G and C are not separated by a permeability-adjusting spacer but enzyme sets S and G are separated by a permeability-adjusting spacer. In yet another embodiment, the enzyme sets G and C are embedded within the same network of polymer brushes. In yet another embodiment, the enzyme sets S, G and C are embedded within the same network of polymer brushes, with no permeability adjusting spacers.

The biosensor 100 may then be inserted into the body of a living being or alternatively it may be placed outside the body of the living being and fluids from the body are transferred to the surroundings of the biosensor 100.

In one embodiment, the biosensor 100 is operated by placing it inside the body of a living being. The biosensor 100 detects the presence or absence of a desired metabolite. The enzyme-containing porous section 116 that lies between the working electrode 106 and the first permeability-adjusting spacer 108 contains a sequence of enzymes that upon being contacted by a metabolite A, leads to a series of reactions catalyzed by $S_1$, $S_2$, and $S_3$ enzymes that produce hydrogen peroxide. The hydrogen peroxide is electrochemically oxidized to generate a signal proportional to the concentration of the metabolite A in subcutaneous tissue, assuming that the reaction intermediates B and C are not present in subcutaneous tissue. The first permeability-adjusting spacer 108 is intended to modulate or exclude permeation of a variety of species.

The second set of enzymes G ($G_1$, $G_2$, $G_3$ . . . ), tend to serve two functions: (i) convert the excess hydrogen peroxide to oxygen, and (ii) store a large amount of oxygen within this layer. This layer provides the desired oxygen supply to drive at least one of the sensing enzymatic reactions within the first section of network of brushes. The third enzyme set C ($C_1$, $C_2$, $C_3$, . . . ) converts the electroactive endogenous species ($I_1$, $I_2$, $I_3$, . . . ) to non-electroactive ones so that they do not contribute to the detected amperometric signal. The oxygen required to drive the enzymatic reactions in the third enzymatic set C, are provided by the action of the second enzymatic set G. In the case that the byproducts of the serial reactions B, C, and then like, are present in the subcutaneous tissue, enzyme $S_2$, $S_3$, and the like, need to be also included in the enzymatic set C within enzyme containing porous section 120. This will ensure that the endogenous species B, C, and the like, are eliminated and do not reach the inner part of the biosensor.

In yet another embodiment, the biosensor can be utilized for continuous, assessment of enzymatic activity. Such enzymatic detection is achieved through a differential measurement of metabolites associated with a particular enzyme. FIGS. 2 and 3 illustrate the disclosed methodology to measure the activity of blood-soluble proteins. FIGS. 2 and 3 are a schematic representation of a multiple set of biosensors, along with various chemical, electro-chemical and diffusion processes that are used in the detection of protein levels through differential measurement of its metabolites. When a blood-soluble protein ($S_1$) comes into contact with metabolite A, it produces a reaction by-product B. The reaction-by product B reacts with enzyme $S_2$ to produce a second reaction by-product C which then reacts with enzyme $S_3$. The reaction between the by-product C and the enzyme $S_3$ leads to an electroactive detectable species such as hydrogen peroxide. The hydrogen peroxide is electrochemically reacted onto the working electrode and its presence is detected by the changes in current produced as result of biasing voltage applied between working electrode 106 and the reference electrode 104.

By assuming that the metabolites A, B and C are present in the body, changes in the activity of enzyme $S_1$ (present in the body) can be assessed by changes in the individual concentrations of analyte A, B and C via a combination of working electrodes shown in FIGS. 2 and 3.

FIG. 2(A) shows the detection of only metabolite A from amongst metabolites A, B and C. In this configuration, the metabolite A present outside the biosensor contacts the enzyme $S_3$ in the enzyme-containing porous section 116 to produce a by-product B, which in turn reacts with enzyme $S_2$ to produce a by-product C, which reacts with enzyme $S_1$ to produce a detectable species. The decomposition of the detectable species results in a change in current produced as result of application of biasing voltage applied between working electrode and the reference electrode. By using a chart or a table that contains relationships between the current at a particular biasing voltage and the amount of the detectable species, the amount of the metabolite A can be determined.

In the FIG. 2(A) the metabolites B and C are reacted with enzymes $S_2$ and $S_3$ in the first (from the outside) enzyme-containing porous section 120 to produce electrochemically inactive species and $H_2O_2$, which is electroactive. Subsequently, the electroactive $H_2O_2$ specie is consumed by the second enzyme set G located in the adjacent enzyme-containing porous section 118 and thus is not permitted to enter the third enzyme-containing porous section S 116 to permeate and get sensed at the working electrode 106. Thus, in such a working electrode configuration, the amounts of the metabolites B and C are not determinable.

Figure 2B:
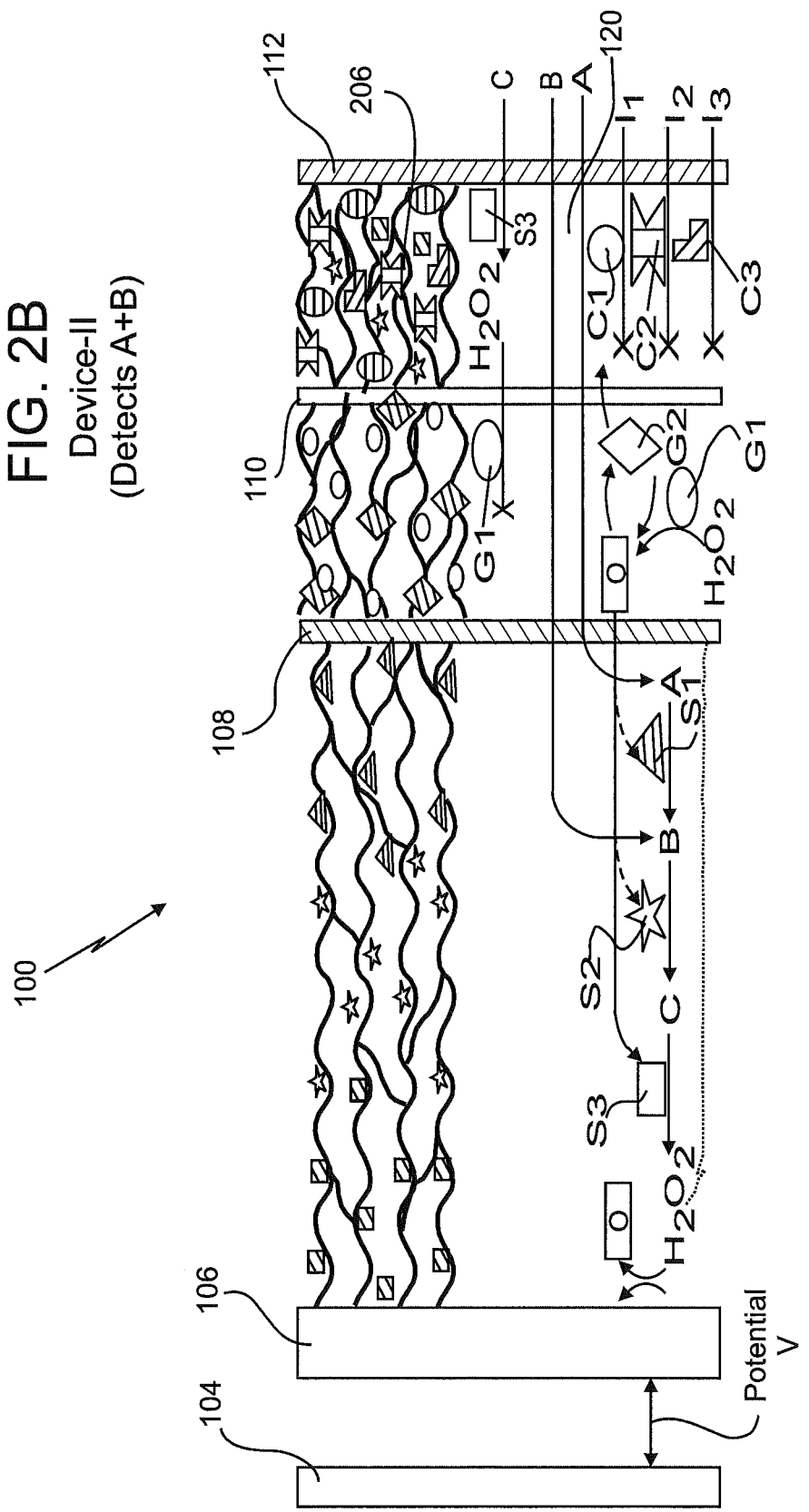
FIG. 2(B) shows the detection of the amounts of the respective metabolites A and B or alternatively the sum of A and B.

In the FIG. 2(B), both the metabolites A and B can permeate through the first, second and third enzyme-containing porous section to enter the enzyme-containing porous section 116 where they react with the enzymes $S_3$, $S_2$ and $S_1$ (for metabolite A) and the enzymes $S_2$ and $S_1$ (for metabolite B) to produce the detectable species that is measured by the biased working electrode. On the other hand, metabolite C permeates only first (from the outside) enzyme-containing porous section 120 and reacts with the enzyme $S_3$ to produce electrochemically inactive species and $H_2O_2$, the latter of which is consumed by the second enzyme set G (located in the adjacent enzyme-containing porous section 118) and thus is not permitted to enter the third enzyme-containing porous section S 116 to permeate and get sensed at the working electrode 106. Such working electrode configuration excludes signal from metabolite C and its generated signal corresponds to the sum of metabolites A and B. By using the biosensor configuration in the FIGS. 2(A) and 2(B), the amounts of the respective metabolites A and B can be determined.

Figure 2C:
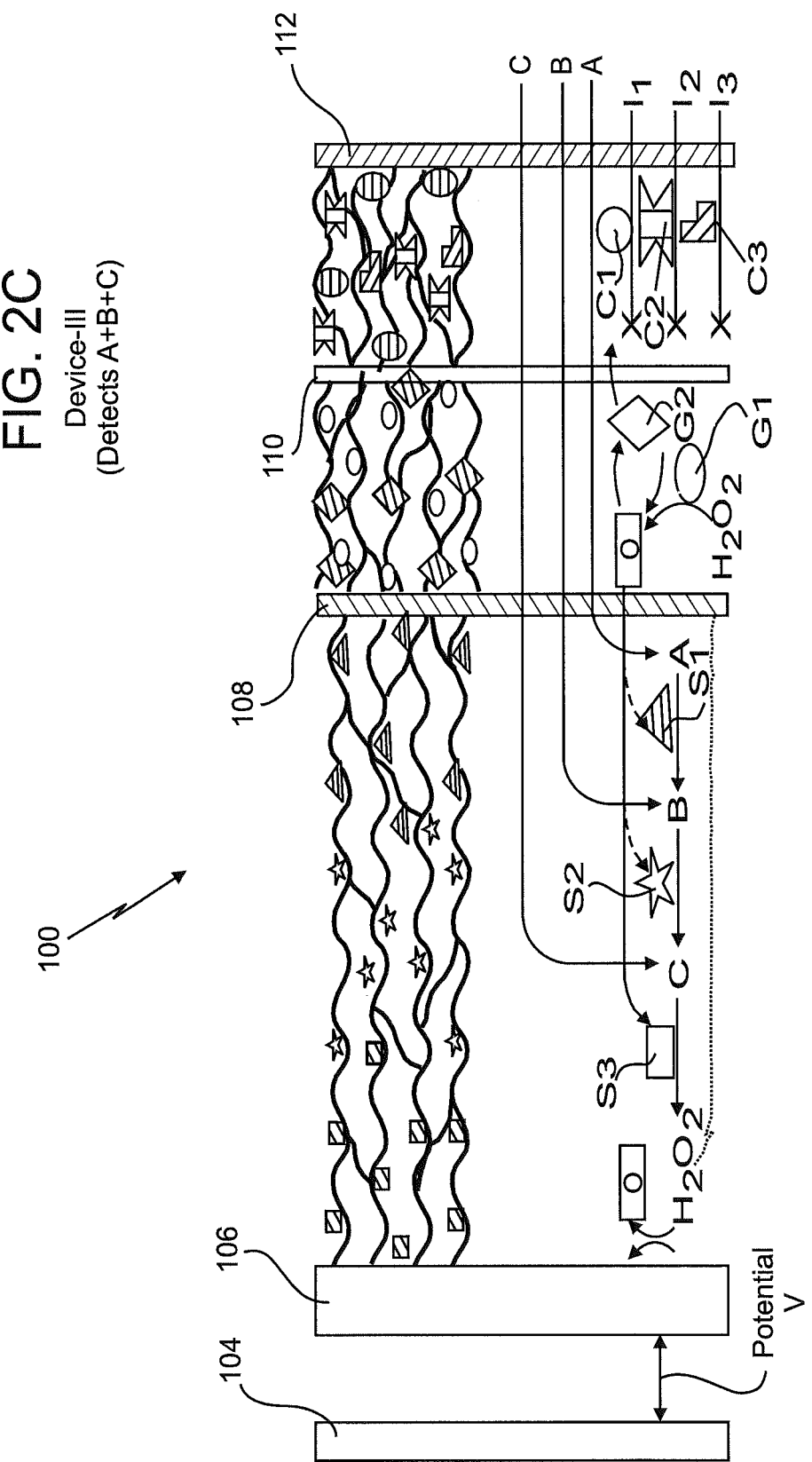
FIG. 2(C) shows the detection of the amounts of the respective metabolites A, B and C or alternatively the sum of A, B and C.

In the FIG. 2(C), all of the metabolites A, B and C can permeate to the enzyme-containing porous section 116 thus producing an amount of the detectable specie that is proportional to the amounts of A and B and C. By using the configuration in the FIGS. 2(A), 2(B) and 2(C), the respective amounts of the metabolites A, B and C may each be determined.

Figure 3A:
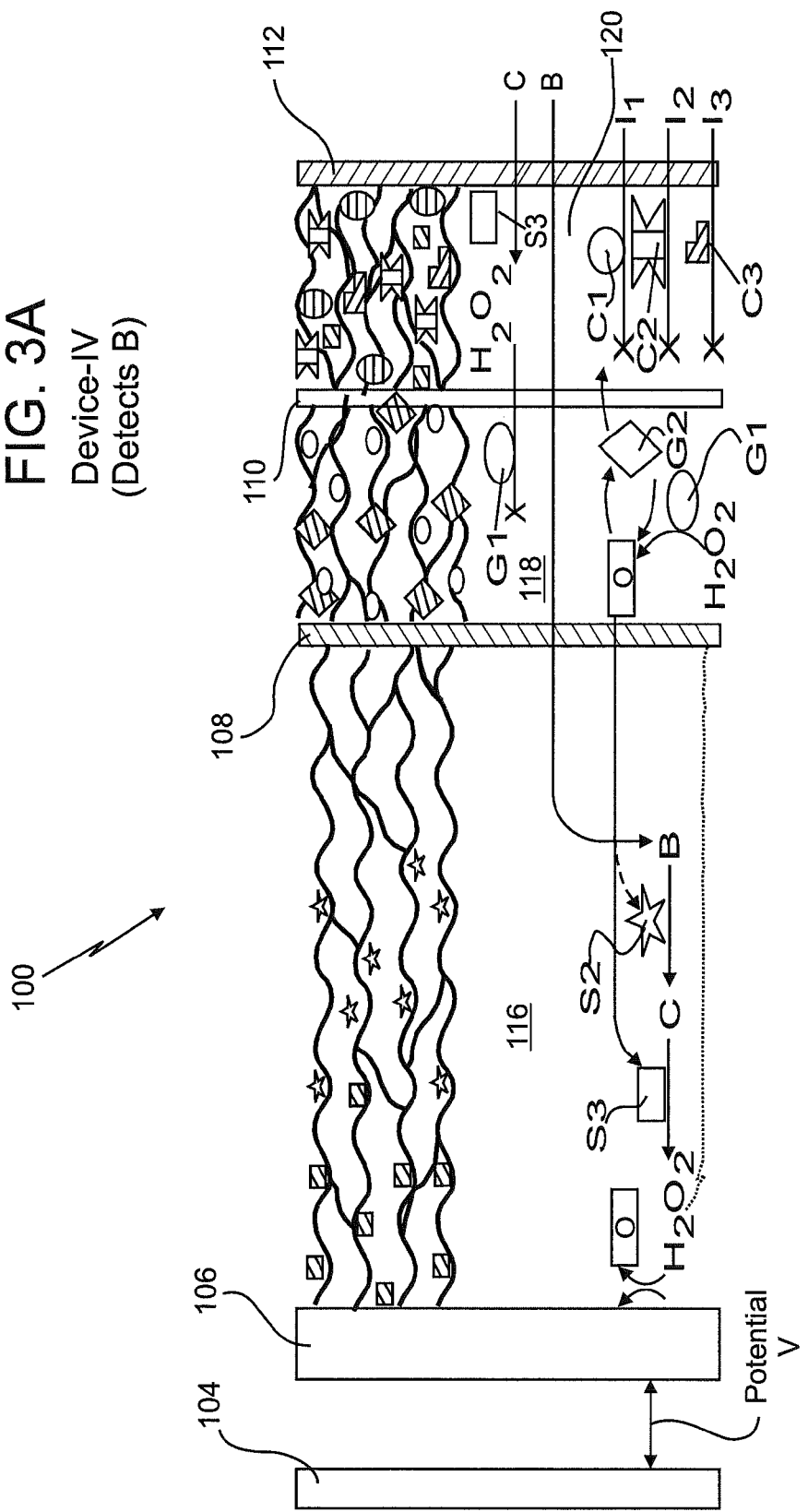
FIG. 3(A) shows the detection of the amount of metabolite B.

In the FIG. 3(A), only the amount of the metabolite B is detected, while in the FIG. 3(B) the sum of the amounts of the metabolite B and C are determined. By combining the configurations of the FIGS. 3(A) and 3(B) the respective amounts of the metabolite B and C can be determined. In the FIG. 3(C), only the amount of the metabolite C is detected.

Thus by selecting the permeability of the respective permeability-adjusting spacers 108, 110 and 112 as well as enzyme-containing porous sections 116, 118, 120 together with the selectively positioning of the enzymes $S_1$, $S_2$ and $S_3$ in the spaces 116, and 120 the amounts of the respective metabolites may be determined. In addition, selective sum of different fractions of the metabolites can also be determined, to provide additional sensing confidence, and extract possible interdependencies among themselves within the sensing configuration.

Thus the response of these 6 configurations (FIGS. 2(A)-(C) and 3(A)-(C)), can be used to determine the relative concentrations of the metabolites A, B or C and can further be fed to a matrix formulation program to find the enzymatic activity of enzymes $S_1$, $S_2$ or $S_3$ adjacent to these sensors or circulating within the blood of a living being.

Another variation of the present invention, the biosensor configuration presented in FIG. 1 can be modified to prevent the tainting of the working electrode from unwanted built up of byproducts. In order to prevent such a byproduct build up, a cooperative removal of byproducts is described in FIG. 4. Similar to the biosensor shown in FIG. 1, the by-products ($bP_A$, $bP_B$, and $bP_C$), from the enzymatic conversion of metabolites A, B and C through $S_1$, $S_2$, and $S_3$ enzymes, respectively, are withdrawn through the by-product removal channel that is in close proximity and within diffusion length with the sensing channel.

Figure 4:
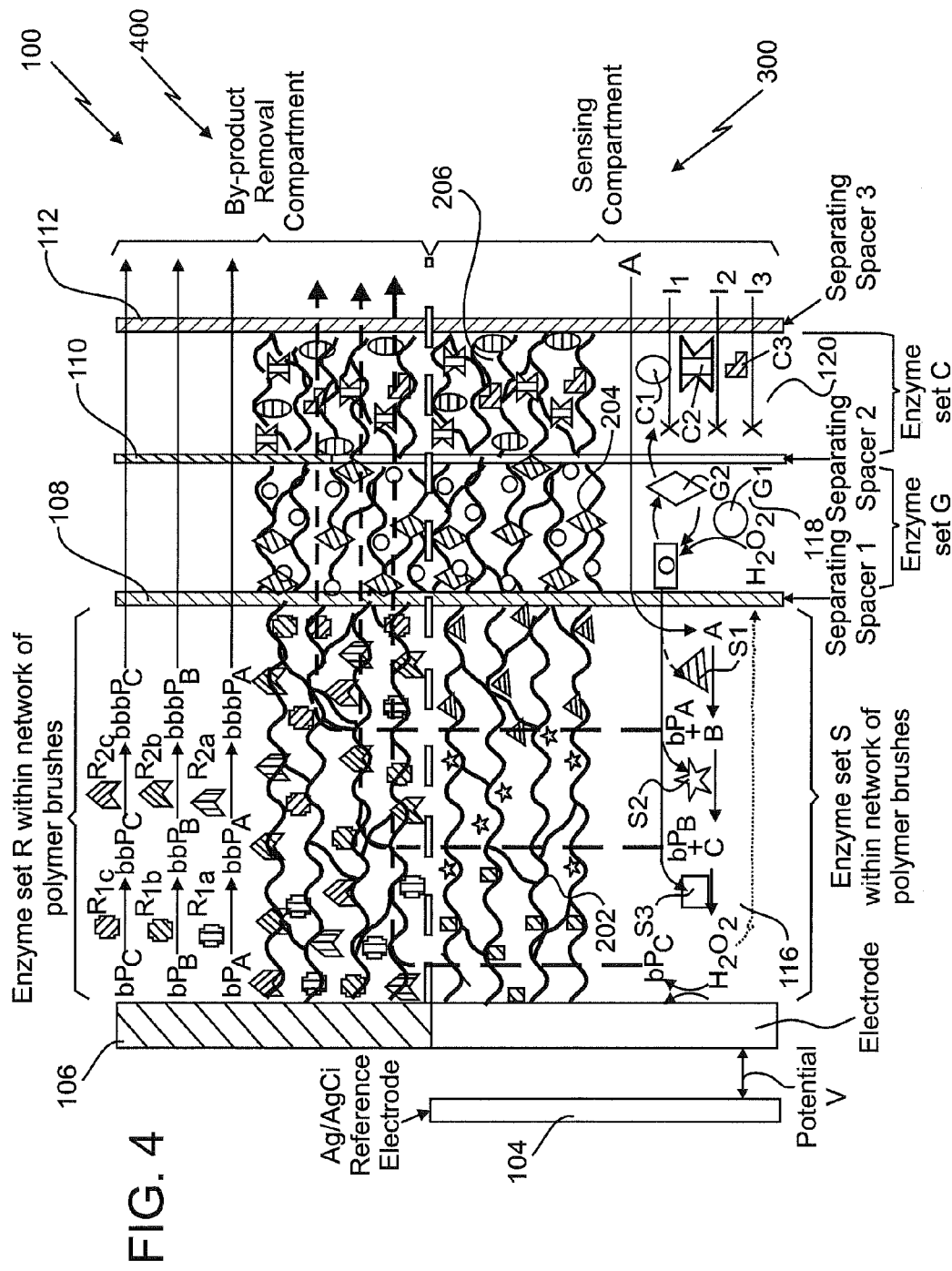
FIG. 4 is a schematic representation of a biosensor devoid of by-product build up. Here, the various chemical, electro-chemical and diffusion processes associated with detection of metabolites as well as the removal of byproducts, are also shown.

The FIG. 4 depicts a biosensor 100 that has two compartments, a first compartment 300 and a second compartment 400. The first compartment 300 and the second compartment 400 are in operative communication with one another. In one embodiment, the first compartment 300 and the second compartment 400 are in fluid communication with one another. In one embodiment, the first compartment 300 and the second compartment 400 are adjacent to one another. The first compartment 300 is similar in construction to the biosensor detailed previously in the FIG. 1. The first compartment 300 and the second compartment 400 are separated by a distance that is less than the mean free path of the byproducts produced as a result of the reactions between the metabolites and the enzymes in the first compartment 300. This proximity between the first compartment and the second compartment facilitates the quick and expeditious removal of the unwanted byproducts.

With respect to the FIG. 4, it may be seen that when the metabolite A reacts with the enzyme $S_1$, a byproduct $bP_A$ is produced. Similarly, byproducts $bP_B$ and $bP_C$ are produced as a result of the interaction of the metabolite B and C with the enzymes $S_2$ and S3 respectively. These byproducts are undesirable and can contaminate the surface of the working electrode 106 thus resulting in false readings or can cause the entire biosensor to malfunction. It is therefore desirable to remove these byproducts with minimal disturbance to the remainder of the functioning biosensor. The FIG. 4 depicts the migration of the byproducts from the first compartment 300 to the second compartment 400 by dotted lines.

The second compartment 400 facilitates the removal of the unwanted byproducts. The second compartment 400 contains catalysts or enzymes (R) that can convert (e.g., dissociate, decompose or degrade) these undesirable byproducts into low molecular weight products (having a molecular weight of less than equal to about 500 grams per mole, specifically less than or equal to about 100 grams per mole, and more specifically less than or equal to about 50 grams per mole) and cause them to be extracted from the biosensor 100. The enzymes or catalysts (R) can be dispersed within the porous sections (e.g., polymer brushes, nanomaterials, porous nanostructured inorganic matrices and combinations thereof).

It is desirable for the enzymes or catalysts (R) in the second compartment 400 to be capable of dissociating the byproducts into small molecules that can be easily discharged from the second compartment. The dimensions of the second compartment should be sufficient to easily expel or discharge the unwanted byproducts without disturbing the normal functioning of the biosensor 100.

As can be seen in the FIG. 4, the by-products $bP_A$, $bP_B$, and $bP_C$ are converted to lower molecular weight species ($bbP_A$, $bbP_B$, $bbP_C$), ($bbbP_A$, $bbbP_B$, $bbbP_C$) and so on, through the enzymatic action of enzymes ($R_{1a}$, $R_{1b}$, $R_{1c}$), ($R_{2a}$, $R_{2b}$, $R_{2c}$), and so on, respectively. The enzymes indicated by the letter R are used to facilitate the dissociation and/or degradation of unwanted byproducts and are transferases, hydrolases, oxidases, peroxidases, kinases, superoxidases, phosphatases, pyrophosphatases, oxygenases, nucleases, lipases, peptidases, transacetylases, hydroxylases, dioxygenases, dehydrogenases, carboxylases, aminases, catalases, phosphohydrolases, diaminases, reductases, synthases, kinases, caspases, methionine synthases, cystathionases, and the like.

It is desirable that at least one of the aforementioned enzymes initiate a reaction with all the byproducts (excepting hydrogen peroxide) of the enzymatic reaction of enzyme set S to produce smaller and smaller molecular weight species that can easily diffuse outwards of the sensor. The reactions to produce smaller molecules that can be discharged can be facilitated by the use of catalysts, temperature and pressure in the second compartment 400.

In one embodiment, the incorporation of enzyme set R within the enzyme sets S, G and C can alleviate the need for the spatial arrangement of the by-product removal channel (i.e., the second compartment). Enzyme stabilizers may also be incorporated along with the enzyme sets in each of the network of polymer brushes.

In another embodiment, by-products ($bP_A$, $bP_B$, and $bP_C$) can be removed via lateral diffusion in adjacent channels that are either open or covered with enzyme sets G and/or C. Similarly, incorporation of enzyme set R within the covering enzyme sets G and C can facilitate such by-product removal.

In a variation to the above methodology, the realization of the removal channels is achieved by phase separation.

Figure 5:
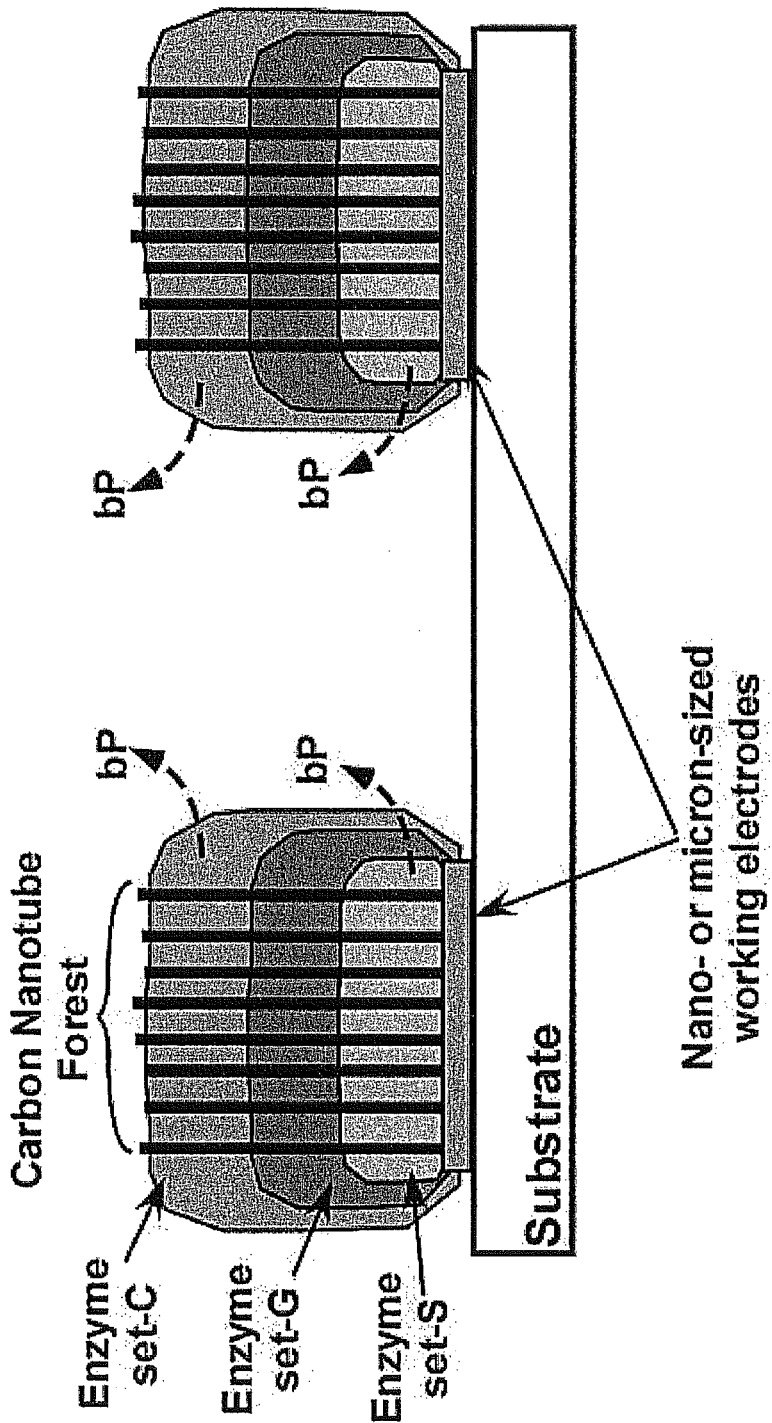
FIG. 5 is an exemplary configuration for the realization of byproduct removal channels using patterned carbon-nanotube forests.

FIG. 5 depicts another embodiment of an exemplary arrangement for the biosensor 100. In this case, the patterning of sensing and by-product removal channels can be realized via templating. In a variation of this methodology, the template can be hexagonally-patterned producing a vertically grown, nanotube forest onto nano- and micro-sized metal electrodes. These porous nanotube forests can enable the selective deposition of a network of brushes that act as the sensing channel, while the lateral openings enable the facile removal of byproducts.

In the FIG. 5, a plurality of nanorods, nanotubes, nanowhiskers, or the like, are disposed on a substrate. The nanorods, nanotubes, nanowhiskers, and the like, have an aspect ratio of greater than or equal to about 50, specifically greater than or equal to about 500, and more specifically greater than or equal to about 5000. In one embodiment, the individual nanorods, nanotubes and/or nanowhiskers are substantially parallel to one another. In another embodiment, the individual nanorods, nanotubes and/or nanowhiskers produce a random network.

A plurality of enzyme layers are disposed upon the substrate and surround at least a portion of the nanorods, nanotubes, nanowhiskers, or the like, as may be seen in the FIG. 5. A first enzyme layer S is disposed on the substrate and encompasses a portion of the nanorods, nanotubes, nanowhiskers, and the like. A second enzyme layer G is then disposed upon the first enzyme layer S, while a third enzyme layer C is then disposed on the second enzyme layer G. The metabolites react with the enzyme layers sequentially or simultaneously to produce detectable species that can be measured and correlated with the concentration of metabolites. In one embodiment, the second enzyme layer G covers the complete upper surface of the first enzyme layer S, while the third enzyme layer C covers the complete upper surface of the second enzyme layer G.

In another embodiment, the redox co-factors of one or more enzymes either enzyme set S can be electrically or electrochemically interfaced with electrically conductive forms of these nanorods, nanotubes and/or nanowhiskers to afford direct electron transfer to enzymes. Such action, simplifies a variety of metabolic pathways and eliminates the formation of a variety of byproducts. In another embodiment, such electron transfer to enzymes can be selectively directed to enzyme set G and/or C, by providing electrical insulation to other respective enzyme regions.

Figure 10:
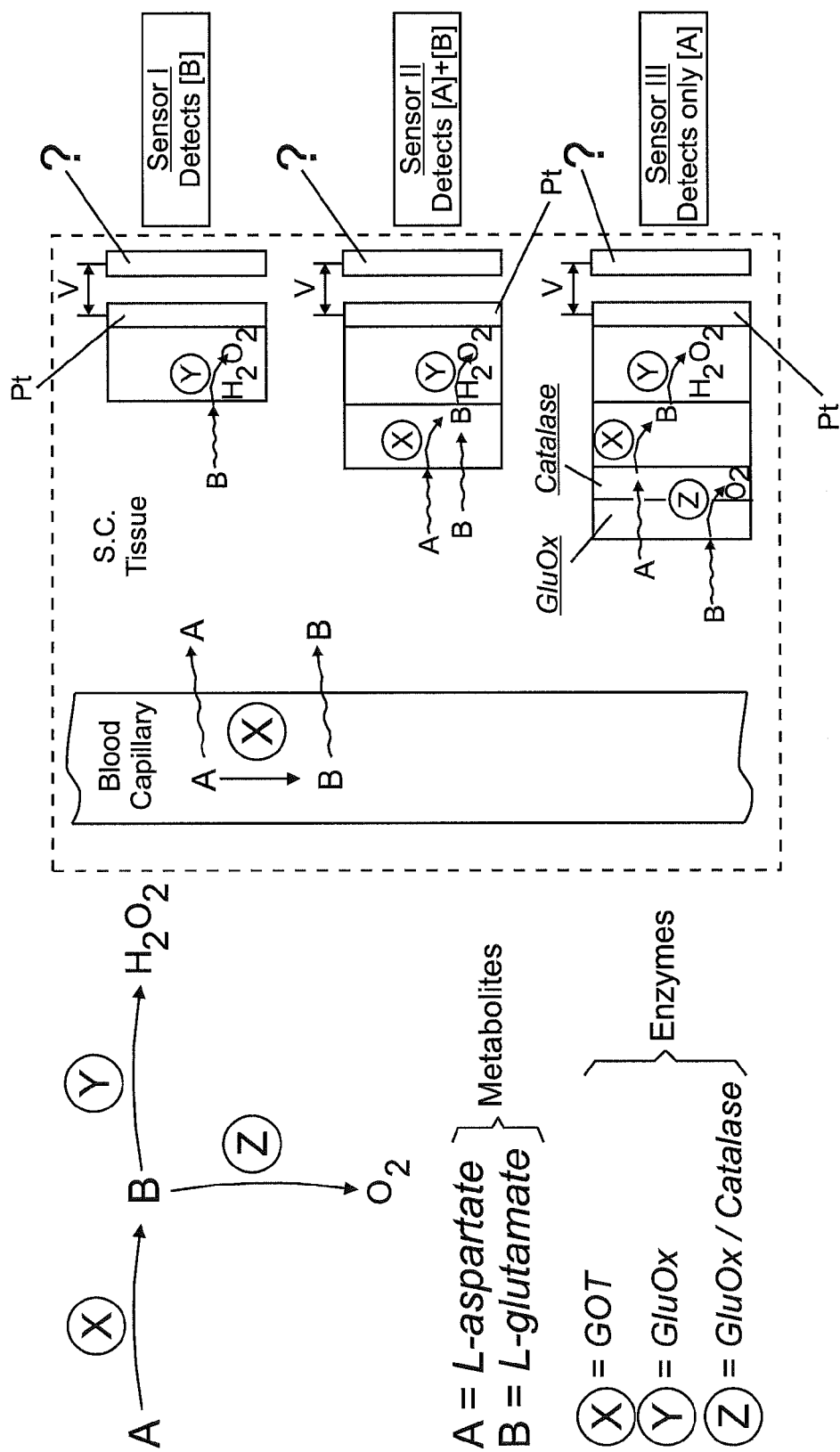
FIG. 10 is a schematic representation of the biosensor set, used to deduce the concentration of glutamic oxaloacetic transaminase (GOT).

In yet another embodiment, depicted in the FIG. 10, the biosensor may be used for a biosensing method for determining the concentration of protein in a sample media. As noted above, the sample media may include the contents of the body of a living being. Here a numbers of biosensors are placed outside a blood vessel (e.g., capillary) that contains enzymes X and metabolites A and B. The sample media is contacted with a plurality of measuring devices (biosensors). The interaction of the enzyme X with the metabolites A and B produce a protein related metabolite whose concentration is related to the concentration of the protein. By making differential measurements of the protein-related metabolite it is possible to determine the concentration of the metabolites and the protein. Each of the measuring devices is interrogated sequentially of concurrently to determine the concentration of the protein-related metabolites. The results from the measuring devices are fed into a matrix formulae. The solution of the matrix formulae facilitates a determination of the concentration of the protein. The protein can be an enzyme, a biomarker, a glycoprotein, a cytokine, a mixture of proteins, or a combination comprising at least one of the foregoing proteins.

The invention will be illustrated in more detail with reference to the following examples, but it should be understood that the present invention is not deemed to be limited thereto. In the following examples a '|' indicate the end of a working electrode 100 or end of either of enzyme containing porous sections 116, 118 or 120 or permeability adjusting spacers 108, 110 or 112. A '+' between two species indicate that the two species are placed in close contact with each other. Species located within parentheses indicate one of the layers 108, 110, 112 or 116, 118, 120 or 202, 204, 206 depicted in FIG. 1.

Example

Example 1

Figure 6:
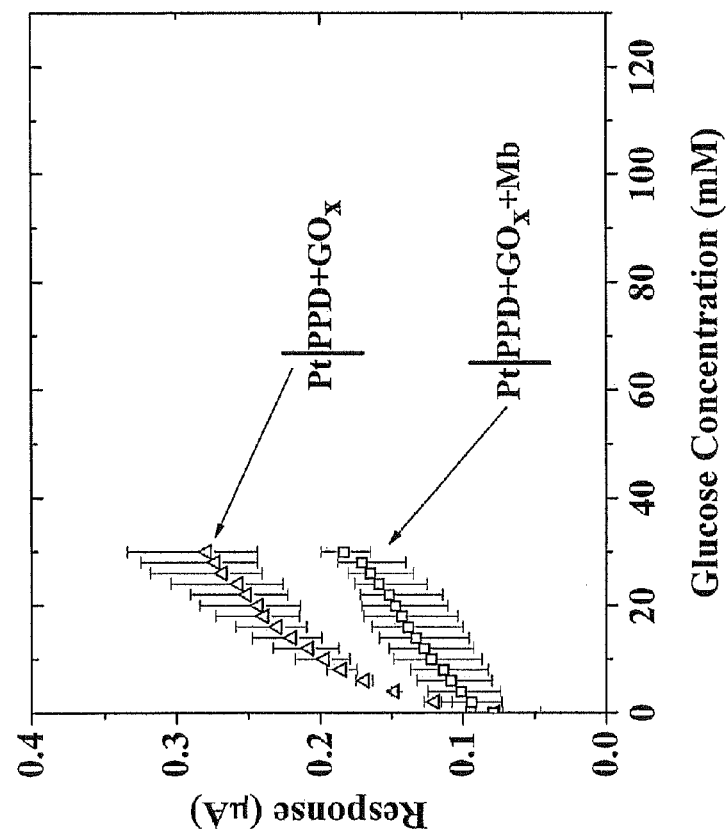
FIG. 6 is a graph of biosensor response containing one ($GO_x$) and two ($GO_x$ and Myoglobin) enzyme sets within a single PPD layer.

This example illustrates a biosensor configuration where the enzyme sets S for sensing glucose oxidase (i.e. $GO_x$) and co-substrate generating/storing G (i.e., myoglobin for $O_2$ storing) are incorporated within the same network of brushes comprised of poly(o-phenylenediamine) (PPD). This biosensor configuration does not possess any permeability-adjusting spacer. FIG. 6 shows the response of a biosensor fabricated using this methodology described specifically for glucose detection. The enzyme sets incorporated network of brushes is a film of poly(o-phenylenediamine) (PPD) that was electropolymerized on the platinum working electrode from a 5 mM o-phenylene diamine (OPD), 25 mg/ml myoglobin (Mb) and 5 mg/ml glucose oxidase ($GO_x$) enzyme solution in aqueous phosphate buffer (pH=8) by applying a constant potential of 0.65 V vs SCE for 15 minute. The configuration of the sensor is Pt|(PPD+Mb+$GO_x$). As can be seen, the glucose sensor with the two enzymes (Mb and $GO_x$) displayed better linearity than the glucose sensor with only one enzyme ($GO_x$). The decreased sensitivity can be understood in terms of incorporating less signal-producing enzyme (i.e. $GO_x$) by the co-addition of Mb.

Example 2

Figure 7:
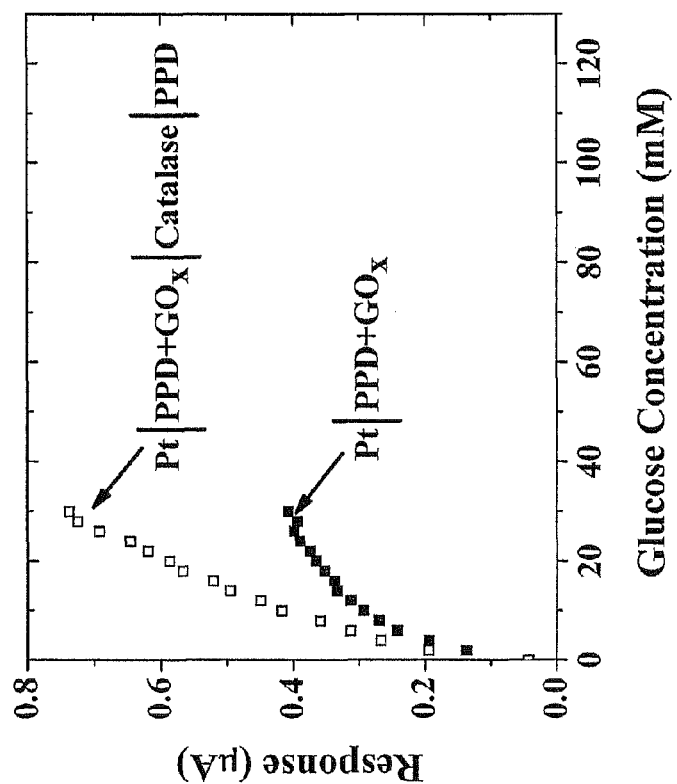
FIG. 7 is a graph of biosensor response containing one ($GO_x$) and two ($GO_x$ and Catalase) enzyme sets, the latter enzyme set being one in which the enzymes are stratified one on top of the other.

FIG. 7 shows the response of a glucose biosensor with two enzyme layers (S and G) and one outer permeability adjusting membrane. The sensor has the following sequence of layers: (a) Glucose oxidase ($GO_x$) incorporated with a network of brushes, achieved via electropolymerization from a 5 mM OPD and 5 milligram per milliliter (mg/ml) $GO_x$ enzyme solution in aqueous buffer solutions (pH=5) by applying a constant potential of 0.65 V vs SCE for 15 minutes; (b) an oxygen-generating enzyme (i.e. catalase) deposited via drop casting; and (c) a permeability-adjusting spacer based on an electropolymerized film of poly(o-phenylene diamine) (PPD) of thickness about 10 nanometers achieved via electropolymerization from a 5 mM o-phenylene diamine (OPD) in an aqueous buffer solutions (pH=7) by applying a constant potential of 0.65 V vs SCE for 15 min. The resulting configuration of the sensor is Pt|(PPD+$GO_x$)|(catalase)|(PPD). As can be seen in FIG. 7, the glucose sensor with two sets of enzymes and a terminal permeability-adjusting spacer displayed better linearity and sensitivity than the corresponding Pt|(PPD+$GO_x$) glucose sensor due to the additional oxygen supply by the catalase containing layer.

Example 3

Figure 8:
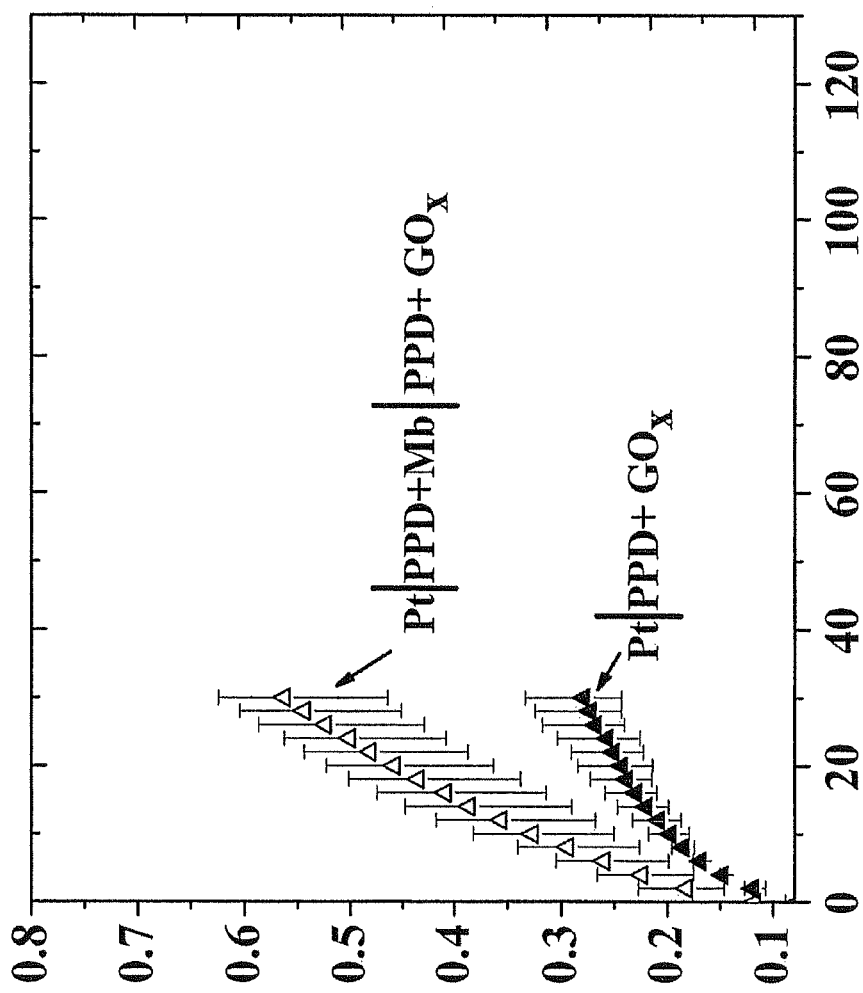
FIG. 8 is a graph showing biosensor response containing one ($GO_x$) and two (Myoglobin and $GO_x$) enzyme sets, the latter enzyme set being one in which the enzymes are stratified one on top of the other.

FIG. 8 shows that the sequence of enzymes sets may also be reverted so that the enzyme set G (i.e., Myoglobin (Mb) for oxygen storage) can be beneath the sensing enzyme set S (i.e., glucose oxidase). This biosensor configuration does not possess any permeability-adjusting spacer. The configuration of the sensor is Pt|(PPD+Mb)|(PPD+$GO_x$), which is achieved with the sequential electropolymerization of PPD brushes on a platinum working electrode in the presence of first myoglobin (Mb) and then glucose oxidase. Here, a 5 mM OPD, where first 25 mg/ml myoglobin (Mb) enzyme was added to the aqueous phosphate buffer (pH=8) of OPD and a constant potential of 0.65 V vs. SCE was applied for 15 minutes. Following rinsing with deionized (DI) water, the second enzyme (glucose oxidase) was incorporated within the PPD network of brushes by electropolymerizing 5 mM of o-phenylene diamine (OPD) in the presence of 5 mg/ml glucose oxidase ($GO_x$) enzyme acetate buffer, by applying a constant potential of 0.65 V vs. SCE for 15 minutes. As can be seen, the glucose sensor with the stratified two layer of enzymes displayed better performance than glucose sensors with only one enzyme set (Pt|(PPD+$GO_x$)), produced under the similar conditions, due to the oxygen-storing capability of myoglobin.

Example 4

Figure 9:
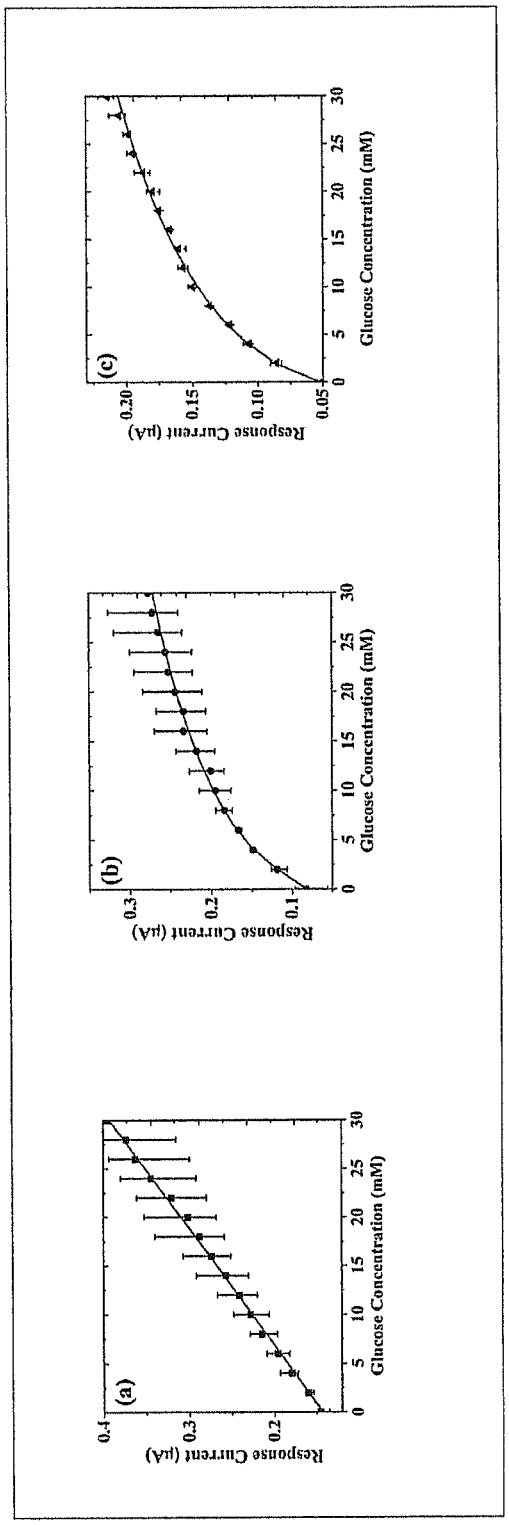
FIGS. 9(A), (B) and (C) are graphs depicting biosensor response containing one ($GO_x$) grown within a PPD network of brushes at a pH of (A) 3, (B) 5, and (C) 7.

This example illustrates a biosensor configuration of the present invention where the pH during electro deposition of the polymer brushes is varied. This biosensor configuration does not possess any permeability-adjusting spacer. FIGS. 9a, 9b, and 9c show the responses of biosensors with only the sensing enzyme set (i.e. $GO_x$ embedded within a PPD brush) where PPD electropolymerization is realized at pH of 3, 5 and 7, respectively. This was achieved via electropolymerization of 5 mM OPD and 5 mg/ml glucose oxidase ($GO_x$) enzyme solution in aqueous buffer solutions with varying pH by applying a constant potential of 0.65 V vs SCE for 15 min. The configuration of the sensor is Pt|(PPD+$GO_x$). As can be seen, the linearity and sensitivity of the glucose sensor can be modulated by varying the pH.

Example 5

FIG. 10 illustrates a methodology to measure glutamic oxaloacetic transaminase (GOT) hereby denoted as X. The activity of GOT can be monitored by monitoring the rate of production of L-glutamate (metabolite B in FIG. 10) based on reaction (6).

(6)

The amount of L-glutamate produced can be electrochemically monitored through its oxidation to $H_2O_2$, using glutamate oxidase (GluOx) (hereby denoted as enzyme Y). Sensor I with enzyme Y can detect the concentration levels of B that diffuses from blood vessels to subcutaneous tissue. By the incorporation of an additional layer containing enzyme X, Sensor II can detect B that corresponds to both unconverted and GOT-converted B. By comparing the response of Sensors I and II, one measure the concentrations of metabolites A and B, as well as standardize the activity of immobilized enzyme X in Sensor II.

With an additional layer of GluOx and catalase (enzyme Z in FIG. 10), Sensor III consumes B (that diffuses inwards from the subcutaneous tissue) and transforms it to oxygen. On the other hand, enzyme Z does not catalyze A which diffuses to the second layer and is converted to B. The majority of B is expected to diffuse to the third layer (Y) and be converted to hydrogen peroxide ($H_2O_2$) allowing it to be electrochemically sensed. This is based on the chemical activity of enzyme Y that drives B towards the platinum (Pt) electrode rather than towards the enzyme Z layer (dotted arrow), where it must first pass the catalase layer (a layer with no chemical affinity for B), before reacting with the outer Y layer. Based on this, the signal of Sensor III is directly proportional to the concentration of A, which is inversely proportional to the concentration of the target enzyme X in the blood capillary. By comparing the responses of all three sensors, the activity of target enzyme X can be determined along with the concentrations of metabolites A and B.

As noted from the examples above, there are a large number of metabolites whose concentrations can be determined using the biosensor. Examples of such metabolites are glucose, lactate, oxygen, glutamate, choline, phosphates, acetylcholine, dioxybutyrate, homocysteine, cysteine, creatine, creatinine, sucrose, fructose, nitric oxide, galactose, arsenite, cholesterol, fructosamine, bilirubin, glycine, methionine, L-citrulline, phosphatidic acid, lysophospatidic acid, arachidonic acid and asymmetric dimethylarginine, 1,3-diaminopropane, 21-deoxycortisol, aminoadipic acid, D-2-hydroxyglutaric acid, L-2-hydroxyglutaric acid, aminoadipic acid, 2-hydroxyadipic acid, oxoadipic acid, oxoglutaric acid, 7-hydroxyprogesterone, 3-hydroxyisovaleric acid, 3-hydroxymethylglutaric acid, 3-methylcrotonylglycine, 3-methylglutaconic acid, adipic acid, ammonia, methylglutaric acid, (S)-3-dydroxyisobutyric acid, 3-hydroxyisovaleric acid, 3-methylcrotonylglycine, 3-hydroxyisovaleric acid, pyruvic acid, (S)-3,4-dihydroxybutyric acid, pyroglutamic acid, ganglioside GM3, glucosylceramide, lactosylceramide, tetrahexosylceramide, trihexosylceramide, 2-hydroxestradiol, 2-hydroxyestrone, 20-hydroxyeicosatetraenoic acid, 5-acetylamino-6-amino-3-methyluracil, alpha-N-phenylacetyl-L-glutamine, androstenedione, benzoic acid, bromide, cadaverine, cholic acid, coproporphyrin I, coproporphyrin III, deoxycholic acid, deoxycytidine, DHEA sulfate, DL-homocystine, estradiol, estriol, estrone, estrone sulfate, fluorine, glycocholic acid, guanine, hexanal, hydroxyphenyllactic acid, iodide, L-aspartic acid, L-cystine, L-glutamine, L-lactic acid, L-malic acid, L-methionine, malondialdehyde, myo-inositol hexakisphosphate, N-acetylaspartylglutamic acid, orotidine, progesterone, salicyluric acid, selenomethionine, thymine, uric acid, vanilpyruvic acid, cortisol, anabasine, cotinine, cydroxycotinine, L(-)-nicotine pestanal, nornicotine, L-lactic acid, heptacarboxylporphyrin I, enkephalin L, 24-hydroxycholesterol, 27-hydroxycholesterol, epinephrine, deoxyadenosine, 1-methyladenine, succinyladenosine, hexacosanoic acid, phytanic acid, pristanic acid, L-pipecolic acid, erucic acid, 7C-aglycone, 5C-aglycone, (R)-salsolinol, alpha-carotene, 5-methyltetrahydrofolic acid, butyric acid, mannitol, meopterin, quinolinic acid, 2-butanol, acetone, butanone, ethanol, isopropyl alcohol, methanol, acetaldehyde, nicotinic acid, pantothenic acid, riboflavin, scyllitol, thiamine, homogentisic acid, aminoadipic acid, L-histidine, 1,5-anhydrosorbitol, 1-methylhistidine, 3,4-dihydroxybenzeneacetic acid, 3-methylhistidine, 4-hydroxy-L-proline, 4-hydroxynonenal, 5-hydroxylysine, 8-hydroxyguanine, 8-hydroxyguanosine, anserine, carnosine, citrulline, dopamine, epsilon-(gamma-glutamyl)-lysine, folic acid, fumaric acid, galactitol, gamma-aminobutyric acid, glycerophosphocholine, glycylproline, hydroxyproline, L-2,4-diaminobutyric acid, L-alpha-aminobutyric acid, L-arabitol, L-arginine, L-asparagine, L-cystathionine, L-DOPA, L-glutamic acid, L-isoleucine, L-leucine, L-lysine, L-phenylalanine, L-proline, L-serine, L-threonine, L-tryptophan, L-tyrosine, L-valine, methylmalonic acid, myoinositol, ornithine, pentosidine, phosphorylcholine, prolylhydroxyproline, ribitol, sorbitol, succinic acid, thiamine monophosphate, thiamine pyrophosphate, estriol 3-sulfate 16-glucuronide, estriol-3-glucuronide, acetylglycine, N-acetylserine, L-thyronine, prostaglandin E2, kynurenic acid, 24,25-dihydroxyvitamin D, 25,26-dihydroxyvitamin D, 25-hydroxyvitamin D2, calcidiol, ergocalciferol, vitamin D3, 11-dehydro-thromboxane B2, 5a-tetrahydrocortisol, ethylmalonic acid, FAD, flavin mononucleotide, glutaric acid, isovalerylglycine, liothyronine, suberic acid, tetrahydrocortisone, thyroxine, 3-hydroxybutyric acid, acetoacetic acid, isocitric acid, L-glutamic acid, L-malic acid, oxalacetic acid, indoleacetic acid, argininosuccinic acid, uracil, 3-methoxytyrosine, 5-mydroxyindoleacetic acid, homovanillic acid, N-acetyl-L-tyrosine, N-acetylvanilalanine, vanillylmandelic acid, vanylglycol, taurocyamine, aspartylglycosamine, 1,3,7-trimethyluric acid, 1,3-dimethyluric acid, 1,7-dimethyluric acid, 1-methylxanthine, 11b-PGF2a, 3-chlorotyrosine, 3-methylxanthine, 5-HETE, 7-methylxanthine, caffeine, paraxanthine, theobromine, theophylline, iodotyrosine, dimethyl-L-arginine, 13S-hydroxyoctadecadienoic acid, symmetric dimethylarginine, androstanediol, trans-trans-muconic acid, 2-methyl-3-hydroxybutyric acid, 2-methylacetoacetic acid, tiglylglycine, acetaminophen glucuronide, ubiquinol, dihydrothymine, ureidoisobutyric acid, chenodeoxycholic acid, chenodeoxycholic acid glycine conjugate, hyaluronic acid, taurochenodesoxycholic acid, taurocholic acid, 1b,3a,12a-trihydroxy-5b-cholanoic acid, hyocholic acid, hyodeoxycholic acid, ursodeoxycholic acid, isoursodeoxycholic acid, lithocholic acid, ursocholic acid, 2-methylcitric acid, 3-methylcrotonylglycine, hydroxypropionic acid, 2-pyrrolidinone, dimethylamine, 8-isoprostane, ascorbic acid, glutathione, o-phosphoethanolamine, 3,5-diiodothyronine, 1,3-diaminopropane, 1-methylguanosine, 16a-hydroxyestrone, enterodiol, enterolactone, N1-acetylspermidine, N8-acetylspermidine, perillic acid, perillyl alcohol, ribothymidine, xanthosine, testosterone, 1-methyluric acid, 3-methyladenine, citric acid, cytidine, hypoxanthine, inosine, N-acetyl-L-aspartic acid, orotic acid, oxidized glutathione, pseudouridine, thymidine, uridine, xanthine, 1-methylinosine, 16a-hydroxydehydroisoandrosterone, 5a-tetrahydro corticosterone, alpha-linolenic acid, alpha-tocopherol, B-carotene, beta-cortol, docosahexaenoic acid, docosapentaenoic acid, gama-tocopherol, linoleic acid, lycopene, putrescine, tetrahydrodeoxycorticosterone, tetrahydrodeoxycortisol, vitamin A, L-fucose, prostaglandin F2a, leukotriene B4, 6-keto-prostaglandin F1a, sebacic acid, butyrylcarnitine, decanoylcarnitine, dodecanoylcarnitine, isovalerylcarnitine, L-hexanoylcarnitine, L-octanoylcarnitine, L-palmitoylcarnitine, lactulose, propionylcarnitine, stearoylcarnitine, tiglylcarnitine, dihydrouracil, 5alpha-cholestanol, lathosterol, 1-methyladenosine, 3,5-diiodo-L-tyrosine, betaine, cyclic AMP, guanidine, guanidinosuccinic acid, guanidoacetic acid, methylguanidine, picolinic acid, 2,3-butanediol, 2-hydroxyphenethylamine, 2-oxoarginine, 4-guanidinobutanoic acid, 7a-hydroxycholesterol, argininic acid, cholesterol sulfate, homo-L-arginine, methanethiol, p-octopamine, propylene glycol, sulfolithocholylglycine, tyramine, urea, L-kynurenine, beta-leucine, cob(I)alamin, inosinic acid, 16-a-hydroxypregnenolone, pyridinoline, histamine, lipoxin A4, hydrogen peroxide, thromboxane A2, D-xylose, 19-hydroxyandrost-4-ene-3,17-dione, glyceric acid, L-a-glutamyl-L-lysine, corticosterone, cortisone, 1-methylhistamine, (R)-3-hydroxybutyric acid, (R)-3-hydroxyisobutyric acid, (S)-3-hydroxyisobutyric acid, 1-butanol, 4-heptanone, D-lactic acid, glycerol, hyaluronan, L-carnitine, pyruvaldehyde, S-adenosylmethionine, hydrogen carbonate, ureidopropionic acid, beta-alanine, cortol, cortolone, leukotriene C4, leukotriene E4, adenosine triphosphate, ADP, guanosine diphosphate, guanosine triphosphate, p-hydroxyphenylacetic acid, taurine, 2-methylbutyrylglycine, isobutyrylglycine, methylsuccinic acid, N-butyrylglycine, epitestosterone, thyroxine sulfate, norepinephrine, etiocholanolone, diphenhydramine, 3-hydroxydodecanoic acid, diadenosine hexaphosphate, diadenosine pentaphosphate, diadenosine tetraphosphate, diadenosine triphosphate, xanthurenic acid, cyanocobalamin, pyridoxine, hydrogen sulfide, thiosulfate, aldosterone 18-glucuronide, p-synephrine, m-tyramine, serotonin, 1-naphthol, 2-naphthol, retinyl ester, 2-pyrocatechuic acid, gentisic acid, dopamine glucuronide, or the like, or a combination comprising at least one of the foregoing metabolites. In one embodiment, the metabolite can be an ion and can comprise hydrogen ions ($H^+$), chlorine ions ($Cl^-$), potassium ions ($K^+$), calcium ions ($Ca^{2+}$), irons ions ($Fe^{3+}$, $Fe^{2-}$), phosphate ions ($PO_4^3$), aluminum ions ($Al^{3+}$), barium ions ($Ba^{2+}$), beryllium ions ($Be^{2+}$), bismuth ions ($Bi^{3-}$), cadmium ions ($Cd^{2+}$), cobalt ions ($Co^{2+}$, $Co^{3+}$), copper ions ($Cu^{2+}$), palladium ions ($Pd^{2+}$), lithium ions ($Li^+$), magnesium ions ($Mg^{2+}$), manganese ions, mercury ions, molybdenum ions, nickel ions, silicon ions, strontium ions, tin ions, titanium ions, tungsten ions, vanadium ions, zinc ions, nitrate ions, chromium ions, or the like, or a combination comprising at least one of the foregoing ions.

While the invention has been described in detail in connection with a number of embodiments, the invention is not limited to such disclosed embodiments. Rather, the invention can be modified to incorporate any number of variations, alterations, substitutions or equivalent arrangements not heretofore described, but which are commensurate with the scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A measuring device for determining the concentration of metabolite in a sample media, comprising:
   a reference electrode;
   a counter electrode;
   a working electrode;
   a first permeability-adjusting spacer; the first permeability adjusting spacer being oppposedly disposed to the working electrode and forming a first enzyme-containing porous section between the working electrode and the first permeability-adjusting spacer, the first enzyme-containing porous section being in direct contact with the working electrode;
   a first set of enzymes the first set of enzymes being disposed on a first porous matrix that is disposed in the first enzyme-containing porous section;
   a second permeability-adjusting spacer; the second separating spacer being oppposedly disposed to the first permeability-adjusting spacer and forming a second enzyme-containing porous section between the first permeability-adjusting spacer and the second permeability adjusting spacer;
   a second set of enzymes; the second set of enzymes being disposed on a second porous matrix that is disposed in the second enzyme-containing porous section;
   a third permeability-adjusting spacer; the third permeability-adjusting spacer being oppposedly disposed to the second permeability-adjusting spacer and forming a third enzyme-containing porous section between the second permeability-adjusting spacer and the third permeability-adjusting spacer;
   a third set of enzymes; the third set of enzymes being disposed on a third porous matrix that is disposed in the third enzyme-containing porous section;
   wherein the first set of enzymes initiates a sequence of reactions that transform the metabolite into an electrochemically active species whose concentration can be sensed by the working electrode;
   wherein the second set of enzymes has the ability to recycle the electrochemically species generated by the first set of enzymes and transform it to a co-substrate for at least one enzyme of the first set of enzymes; and wherein the second set of enzymes has an ability to store excess of the co-substrate and provide it to the first set of enzymes as well as the third set of enzymes;
   wherein the third set of enzymes converts interfering electrochemically active species into electrochemically inactive byproducts in conjunction with the co-substrate stored in the second set of enzymes; wherein the third set of enzymes contains a portion of enzymes from the first set of enzymes to prevent by-products of the enzymatic sequence of reactions established by first set of enzymes that are present in the sample media to diffuse inwards and contribute to a production of the electrochemically active species that is sensed by the working electrode; and wherein the permeability-adjusting spacers assist in controlling diffusion of the metabolite, its enzymatic byproducts, co-substrates and interfering electrochemically active species through the first enzyme containing porous section, the second enzyme containing porous section and the third enzyme containing porous section in order to establish operative detection of metabolite over a range of concentration and minimum signal from other metabolites and interfering electrochemically active species.

2. The measuring device of claim 1, further comprising a fourth set of enzymes; the fourth set of enzymes being added to assist with the removal of enzymatic byproducts from said first, second and third enzyme-containing porous sections.

3. The measuring device of claim 1, further comprising the formation of a plurality of vertical cavities throughout the first enzyme containing porous section, the second enzyme containing porous section and the third enzyme containing porous section.

4. The measuring device of claim 1, where the first permeability adjusting spacer, the second permeability adjusting spacer and the third permeability adjusting spacer assist with the removal of enzymatic byproducts from said first enzyme containing porous section, the second enzyme-containing porous section and/or the third enzyme-containing porous section.

5. The measuring device of claim 1, where the electrochemically active species is $H_2O_2$.

6. The measuring device of claim 1, where the co-substrate is oxygen.

7. The measuring device of claim 1, where the sample media is a sample fluid, a body fluid, a tissue fluid or serum.

8. The measuring device of claim 1, where the sample media is the body of a living being.

9. The measuring device of claim 1, where the metabolite is glucose, lactate, oxygen, glutamate, choline, phosphate, acetylcholine, dioxybutyrate, homocysteine, cysteine, creatine, creatinine, sucrose, fructose, nitric oxide, galactose, arsenite, cholesterol, fructosamine, bilirubin, glycine, methionine, L-citrulline, phosphatidic acid, lysophospatidic acid, arachidonic acid, asymmetric dimethylarginine, 1,3-diaminopropane, 21-deoxycortisol, aminoadipic acid, D-2-hydroxyglutaric acid, L-2-hydroxyglutaric acid, aminoadipic acid, 2-hydroxyadipic acid, oxoadipic acid, oxoglutaric acid, 7-hydroxyprogesterone, 3-hydroxyisovaleric acid, 3-hydroxymethylglutaric acid, 3-methylcrotonylglycine, 3-methylglutaconic acid, adipic acid, ammonia, methylglutaric acid, (S)-3dydroxyisobutyric acid, 3-hydroxyisovaleric acid, 3-methylcrotonylglycine, 3-hydroxyisovaleric acid, pyruvic acid, (S)-3,4-dihydroxybutyric acid, pyroglutamic acid, ganglioside GM3, glucosylceramide, lactosylceramide, tetrahexosylceramide, trihexosylceramide, 2-hydroxyestradiol, 2-hydroxyestrone, 20-hydroxyeicosatetraenoic acid, 5-acetylamino-6-amino-3-methyluracil, alpha-N-phenylacetyl-L-glutamine, androstenedione, benzoic acid, bromide, cadaverine, cholic acid, coproporphyrin I, coproporphyrin III, deoxycholic acid, deoxycytidine, DHEA sulfate, DL-homocystine, estradiol, estriol, estrone, estrone sulfate, fluorine, glycocholic acid, guanine, hexanal hydroxyphenyllactic acid, iodide, L-aspartic acid, L-cystine, L-glutamine, L-lactic acid, L-malic acid, L-mefhionine, malondialdehyde, myo-inositol hexakisphosphate, N-acetylaspartylglutamic acid, orotidine, progesterone, salicyluric acid, selenomethionine, thymine, uric acid, vanilpyruvic acid, Cortisol, anabasine, cotinine, cydroxycotinine, L(–)-nicotine pestanal nornicotine, L-lactic acid, heptacarboxylporphyrin I, enkephalin L, 24-hydroxycholesterol, 27-hydroxycholesterol, epinephrine, deoxyadenosine, 1-methyladenine, succinyladenosine, hexacosanoic acid, phytanic acid, pristanic acid, L-pipecolic acid, erucic acid, 7C-aglycone, 5C-aglycone, (R)-salsolinol, alpha-carotene, 5-meflyvltetrahydrofolic acid, butyric acid, mannitol meopterin, quinolinic acid, 2-butanol, acetone, butanone, ethanol, isopropyl alcohol, methanol, acetaldehyde, nicotinic acid, pantothenic acid, riboflavin, scyllitol, thiamine, homnogentisic acid, aminoadipic acid, L-histidine, 1,5-anhydrosorbitol, 1-methylhistidine, 3,4-dihydroxybenzeneacetic acid, 3-methylhistidine, 4-hydroxy-L-proline, 4-hydroxynonenal, 5-hydroxylysine, 8-hydroxyguanine, 8-hydroxyguanosine, anscrine, carnosine, citrulline, dopamine, epsilon-(gamma-glutamyl)-lysine, folic acid, fumaric acid, galactitol, gamma-aminobutyric acid, glycerophosphocho line, glycylproline, hydroxyproline, L-2,4-diaminobutyric acid, L-alpha-aminobutyric acid, L-arabitol, L-arginine, L-asparagine, L-cystathionine, L-DOPA, L-glutamic acid, L-isoleucine, L-leucine, L-lysine, L-phenylalanine, L-proline, L-serine, L-threonine, L-tryptophan, L-tyrosine, L-valine, methylmalonic acid, myoinositol, ornithine, pentosidine, phosphorylcholine, prolylhydroxyproline, ribitol, sorbitol, succinic acid, thiamine monophosphate, thiamine pyrophosphate, estrioB-sulfate 16-glucuronide, estriol-3-glucuronide, acetylglycine, N-acetylscrine, L-thyronine, prostaglandin E2, kynurenic acid, 24,25-dihydroxyvitamin D, 25,26-dihydroxyvitamin D, 25-hydroxyvitamin D2, calcidiol, ergocalciferol, vitamin D3, 11-dehydro-thromboxane B2, 5a-tetrahydrocortisol, ethylmalonic acid, FAD, flavin mononucleotide, glutaric acid, isovalerylglycine, liothyronine, suberic acid, tetrahydrocortisone, thyroxine, 3-hydroxybutyric acid, acetoacetic acid, isocitric acid, L-glutamic acid, L-malic acid, oxalacetic acid, indolcacetic acid, argininosuccinic acid, uracil, 3-methoxytyrosine, 5-mydroxyindoleacetic acid, homovanillic acid, N-acetyl-L-tyrosine, N-acetylvanilalanine, vanillylmandelic acid, vanylglycol, taurocyamine, aspartylglycosamine, 1,3,7-trimethyluric acid, 1,3-dimethyluric acid, 1,7-dimethyluric acid, 1-methylxanthine, 1 lb-PGF2a, 3-chlorotyrosine, 3-methylxanfhine, 5-HETE, 7-methylxanthine, caffeine, paraxanthine, theobromine, theophylline, iodotyrosine, dimethyl-L-arginine, 13S hydroxyoctadecadienoic acid, symmetric dimethylarginine, androstanediol, trans-trans-muconic acid, 2-methyl-3-hydroxybutyric acid, 2-methylacetoacetic acid, tiglylglycine, acetaminophen glucuronide, ubiquinol, dihydrothymine, urcidoisobutyric acid, chenodeoxycholic acid, chenodeoxycholic acid glycine conjugate, hyaluronic acid, taurochenodesoxycholic acid, taurocholic acid, 1b,3a,12a-trihydroxy-5b-cholanoic acid, hyocholic acid, hyodeoxycholic acid, ursodeoxycholic acid, isoursodeoxycholic acid, lithocholic acid, ursocholic acid, 2-methylcitric acid, 3-methylcrotonylglycine, hydroxypropionic acid, 2-pyrrolidinone, dimethylamine, 8-isoprostane, ascorbic acid, glutathione, o-phosphoethanolamine, 3,5-diiodothyronine, 1,3-diaminopropane, 1-methylguanosine, 16α-hydroxy estrone, enterodiol, enterolactone, Nl-acetylspermidine, N8-acetylspermidine, perillic acid, perillyl alcohol, ribothymidine, xanthosine, testosterone, 1-methyluric acid, 3-methyladenine, citric acid, cytidine, hypoxanthine, inosine, N-acetylL-aspartic acid, orotic acid, oxidized glutathione, pseudouridine, thymidine, uridine, xanthine, 1-methylinosine, 16ahydroxydehydroisoandrosterone, 5a-tetrahydrocorticosterone, alpha-linolenic acid, alpha-tocopherol, B-carotene, beta-cortol, docosahexaenoic acid, docosapentaenoic acid, gama-tocopherol, linoleic acid, lycopene, putrescine, tetrahydrodeoxycorticosterone, tetrahydrodeoxycortisol, vitamin A, L-fucose, prostaglandin F2a, leukotriene B4, 6-keto-prostaglandin Fla, sebacic acid, butyrylcarnitine, decanoylcarnitine, dodecanoylcarnitine, isovalerylcarnitine, L-hexanoylcarnitine, L-octanoylcarnitine, L-palmitoylcarnitine, lactulose, propionylcarnitine, stearoylcarnitine, tiglylcarnitine, dihydrouracil, 5alphacholestanol, lathosterol, 1-methyladenosine, 3,5-diiodo-Ltyrosine, betaine, cyclic AMP, guanidine, guanidinosuccinic acid, guanidoacetic acid, methylguanidine, picolinic acid, 2,3-butanediol, 2-hydroxyphenethylamine, 2-oxoarginine, 4-guanidinobutanoic acid, 7a-hydroxycholesterol, argininic acid, cholesterol sulfate, homo-L-arginine, methanethiol, p-octopamine, propylene glycol, sulfolithocholylglycine, tyramine, urea, L-kynurenine, beta-leucine, cob(I)alamin, inosinic acid, 16-a-hydroxypregnenolone, pyridinoline, histamine, lipoxin A4, hydrogen peroxide, thromboxane A2, D-xylose, 19-hydroxyandrost-4-ene-3,17-dione, glyceric acid, L-a-glutamyl-L-lysine, corticosterone, cortisone, 1-methylhistamine, (R)-3-hydroxybutyric acid, (R)-3-hydroxyisobutyric acid, (S)-3-hydroxyisobutyric acid, 1-butanol, 4-heptanone, D-lactic acid, glycerol, hyaluronan, L-carnitine, pyruvaldehyde, S-adenosylmefhionine, hydrogen carbonate, ureidopropionic acid, beta-alanine, cortol, cortolone, leukotriene C4, leukotriene E4, adenosine triphosphate, ADP, guanosine diphosphate, guanosine triphosphate, p-hydroxyphenylacetic acid, taurine, 2-methylbutyrylglycine, isobutyrylglycine, methylsuccinic acid, N-butyrylglycine, epitestosterone, thyroxine sulfate, norepinephrine, etiocholanolone, diphenhydramine, 3-hydroxydodecanoic acid, diadenosine hexaphosphate, diadenosine pentaphosphate, diadenosine tetraphosphate, diadenosine triphosphate, xanthurenic acid, cyanocobalamin, pyridoxine, hydrogen sulfide, thiosulfate, aldosterone 18-glucuronide, p-synephrine, m-tyramine, serotonin, 1-naphthol, 2-naphthol, retinyl ester, 2-pyrocatechuic acid, gentisic acid, dopamine glucuronide, isomaltose, melanin, N2,N2-dimethylguanosine, phenylacetic acid, trimethylamine N-oxide and a combination comprising at least one of the foregoing metabolites.

10. The measuring device of claim 1, where the metabolite comprises an ion.

11. The measuring device of claim 10, where the wherein the ion is a hydrogen ion, a chlorine ion, a potassium ion, a calcium ion, an irons ion, a phosphate ion, an aluminum ion, an barium ion, a beryllium ion, a bismuth ion, a cadmium ion, a cobalt ion, a copper ion, a palladium ion, a lithium ion, a magnesium ion, a manganese ion, a mercury ion, a molybdenum ion, a nickel ion, a silicon ion, a strontium ion, a tin ion, a titanium ion, a tungsten ion, a vanadium ion, a zinc ion, a nitrate ion, a chromium ion, or a combination comprising at least one of the foregoing ions.

12. The measuring device of claim 1, where the working electrode comprises a metal or a carbonaceous material; where the metal is platinum, gold, silver, rhodium, iridium or a combination comprising at least one of the foregoing metals.

13. The measuring device of claim 12, where the carbonaceous material comprises carbon nanotubes, carbon black, graphite, graphene sheets, or a combination comprising at least one of the foregoing carbonaceous materials.

14. The measuring device of claim 1, where the working electrode comprises metals that are in nanosized forms: the nanosized forms being nanotubes, nanorods, nanowhiskers, nanoonions, nanohorns, nanoparticles, nanoplatelets or a combination comprising at least one of the foregoing nanosized forms.

15. The measuring device of claim 1, where the working electrode is covered with a permeability adjusting membrane to limit diffusion of molecules larger than $H_2O_2$ towards the said working electrode.

16. The measuring device of claim 15, where the permeability adjusting membrane is an electropolymerized film.

17. The measuring device of claim 16, where the electropolymerized film is composed by a conducting polymer and its composites with biological mediators, nanotubes, graphene, nanoparticles, nanorods, nanowhiskers, nanoonions, nanohorns, nanoplatelets and mixtures thereof.

18. The measuring device of claim 17, where the conducting polymer and its composites is composed by poly(o-phenylene diamine) and its composites with flavin mononucleotide wrapped single walled carbon nanotubes.

19. The measuring device of claim 1, where the first set of enzymes, the second set of enzymes and the third set of enzymes are hydrolases, transferases, reductases, oxidases, polymerases, kinases, transferases, peroxidases, kinases, superoxidases, phosphatases, pyrophosphatases, oxygenases, nucleases, lipases, peptidases, transacetylases, hydroxylases, dioxygenases, dehydrogenases, carboxylases, aminases, catalases, phosphohydrolases, diaminases, reductases, synthases, kinases, caspases, methionine synthase, cystathionases, or a combination comprising at least one of the foregoing enzymes.

20. The measuring device of claim 1, where the first set of enzymes are transferases, hydrolases, oxidases, peroxidases, kinases, superoxidases, phosphatases, or a combination comprising at least one of the foregoing enzymes.

21. The measuring device of claim 1, where the first set of enzymes initiates a reaction sequence with the metabolite of choice to produce hydrogen peroxide.

22. The measuring device of claim 1, where the second set of enzymes are transferases, hydrolases, oxidases, peroxidases, kinases, superoxidases and phosphatases or a combination comprising at least one of the foregoing enzymes.

23. The measuring device of claim 1, where the second set of enzymes comprise two or more enzymes, one of which is operative to store oxygen and release it in oxygen deficient conditions, while the other is operative to generate oxygen.

24. The measuring device of claim 23, where the second set of enzymes comprise myoglobin and catalase.

25. The measuring device of claim 1, where the third set of enzymes are transferases, hydrolases, oxidases, peroxidases, kinases, superoxidases, phosphatases, pyrophosphatases, oxygenases, nucleases, lipases, peptidases, transacetylases, hydroxylases, dioxygenases, dehydrogenases, carboxylases, aminases, catalases, phosphohydrolases, diaminases, reductases, synthases, kinases, caspases, methionine synthase, cystathionases, or a combination comprising at least one of the foregoing enzymes.

26. The measuring device of claim 1, where the first enzyme containing porous section, second enzyme containing porous section, and third enzyme containing porous section each comprise a network of polymer brushes.

27. The measuring device of claim 26, where the network of polymer brushes comprises water soluble polymers; the water soluble polymers being polyethylene oxide, polyvinyl acetate, hydroxypropylcellulose, polyvinyl alcohol, polyhexaethyl methacrylate, polyallyl amine, poly(hyaluronic acid), chitosan, polysugars, polyitaconic acid, or a combination comprising at least one of the foregoing water soluble polymers.

28. The measuring device of claim 26, where the network of polymer brushes comprises of a network of porous conductive materials.

29. The measuring device of claim 26, where the network of polymer brushes comprises water soluble forms of intrinsically conducting polymers; the intrinsically conducting polymers being polyaniline, substituted polyanilines, polypyrroles, substituted polypyrroles, polythiophenes, substituted polythiophenes, polyacetylenes, polyethylene dioxythiophenes, polyethylenedioxypyrroles, polyp-phenylene vinylenes, polycarbazoles, substituted polycarbazoles, polyindoles, poly(o-phenylene diamine)s or a combination comprising at least one of the foregoing intrinsically conducting polymers.

30. The measuring device of claim 26, where the network of polymer brushes is a network of porous conductive materials; the network of porous conductive materials being realized by electropolymerization of o-phenylene diamine, pyrrole, aniline, aniline, sulfonated aniline, sulfonated thiophenes, flavin mononucleotide, substituted anilines, substituted pyrroles, substituted thiophenes, acetylenes, polyethylene dioxythiophenes, ethylenedioxypyrroles, phenylene vinylenes, carbazoles, substituted carbazoles, indoles, carboxy-functionalized aqueously dispersed carbon nanotubes, flavin mononucleotide coated single wall carbon nanotubes, aqueous dispersed nanoparticles with aniline functionalities, and zirconium phosphate nanoplatelets with aniline functionalities.

31. The measuring device of claim 26, where the electropolymerized network of porous conductive materials is sequentially conducted in the presence of the desired enzyme or mixture of enzymes to lead in stratified layers of enzyme contained porous conductive materials.

32. The measuring device of claim 26, where the network of polymer brushes is a network of porous conductive materials; the network of porous conductive materials being realized by electropolymerization of monomers; where the electropolymerized monomers are further grafted with a polyethylene oxide oligomer.

33. The measuring device of claim 26, where the network of polymer brushes comprises a vertical forest of nanorods attached at one of their two ends on the working electrode.

34. The measuring device of claim 33, where the nanorod forest is made of carbon nanotubes.

35. The measuring device of claim 1, wherein the first permeability-adjusting spacer, the second permeability-adjusting spacer and the third permeability-adjusting spacer comprise an organic polymer.

36. The measuring device of claim 35, where the organic polymer is a polyacetal, a polyolefin, a polyacrylic, a polycarbonate, a polystyrene, a polyester, a polyamide, polyamideimides, a polyarylate, a polyarylsulfone, a polyethersulfone, a polyphenylene sulfide, a polyvinyl chloride, a polyethylene oxide, a polysulfone, a polyimide, a polyetherimide, a polytetrafluoroethylene, a polyetherketone, a polyether etherketone, a polyether ketone ketone, a polybenzoxazole, a polyphthalide, a polyacetal, a polyanhydride, a polyvinyl ether, a polyvinyl thioether, a polyvinyl alcohol, a polyvinyl ketone, a polyvinyl halide, a polyvinyl nitrile, a polyvinyl ester, a polysulfonate, a polysulfide, a poly(allyl amine), a polythioester, a polysulfone, a polysulfonamide, a polyurea, a polyphosphazene, a polysilazane, a polyvinyl chloride, a polyvinyl acetate, a humic acid, a cellulose acetate, a polythiophene, a polyphenylene diamine, a polypyrrole, a polynaphthalene a polyurethane, an ethylene propylene diene rubber, a polytetrafluoroethylene, a fluorinated ethylene propylene, a perfluoroalkoxyethylene, a polychlorotrifluoroethylene, a polyvinylidene fluoride, a polysiloxane, or a combination comprising at least one of the foregoing organic polymers.

37. The measuring device of claim 35, where the organic polymer is poly(o-phenylene diamine).

38. The measuring device of claim 35, where the organic polymer is realized by electropolymerization from a water solution containing one or more monomers selected from o-phenylene diamine, pyrrole, aniline, aniline, sulfonated aniline, sulfonated thiophenes, flavin mononucleotide, substituted anilines, substituted pyrroles, substituted thiophenes, acetylenes, polyethylene dioxythiophenes, ethylenedioxypyrroles, phenylene vinylenes, carbazoles, substituted carbazoles, indoles, carboxy-functionalized aqueously dispersed carbon nanotubes, flavin mononucleotide coated single wall carbon nanotubes, aqueous dispersed nanoparticles with aniline functionalities, and a combination comprising at least one of the foregoing monomers.

39. The measuring device of claim 2, where the fourth set of enzymes are transferases, hydrolases, oxidases, peroxidases, kinases, superoxidases, phosphatases, pyrophosphatases, oxygenases, nucleases, lipases, peptidases, transacetylases, hydroxylases, dioxygenases, dehydrogenases, carboxylases, aminases, catalases, phosphohydrolases, diaminases, reductases, synthases, kinases, caspases, methionine synthase, cystathionases, or a combination comprising at least one of the foregoing enzymes.

40. The measuring device of claim 39, where the fourth set of enzymes is distributed within the first enzyme containing porous section, second enzyme containing porous section, and third enzyme containing porous section, or in a combination comprising at least one of the first enzyme containing porous section, the second enzyme containing porous section, and the third enzyme containing porous section.

41. The measuring device of claim 2, where the said fourth set of enzymes is distributed within hydrogels that impregnate and fills a plurality of vertical cavities throughout the first enzyme containing porous section, the second enzyme containing porous section and the third enzyme containing porous section and/or the first permeability adjusting spacer, the second permeability adjusting spacer and the third permeability adjusting spacer.

42. The measuring device of claim 1, where the at least one of the first enzyme containing porous section, the second enzyme containing porous section and the third enzyme containing porous section and/or the first permeability adjusting spacer, the second permeability adjusting spacer and the third permeability adjusting spacers can be deposited by spin coating, drop casting, dip coating, knife coating, spray coating, inkjet printing, or electropolymerization.

43. The measuring device of claim 38, where electropolymerization of o-phenylene diamine is performed at different pHs.

* * * * *